United States Patent
Schlifke-Poschalko

(10) Patent No.: US 8,951,508 B2
(45) Date of Patent: *Feb. 10, 2015

(54) COMPOUND

(75) Inventor: Alexander Schlifke-Poschalko, Basel (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/510,116

(22) PCT Filed: Dec. 8, 2010

(86) PCT No.: PCT/EP2010/069181
§ 371 (c)(1),
(2), (4) Date: Oct. 15, 2012

(87) PCT Pub. No.: WO2011/070073
PCT Pub. Date: Jun. 16, 2011

(65) Prior Publication Data
US 2013/0034511 A1    Feb. 7, 2013

(30) Foreign Application Priority Data

Dec. 9, 2009  (EP) .................................... 09178503

(51) Int. Cl.
| | | |
|---|---|---|
| *A61Q 17/04* | (2006.01) | |
| *A61K 8/69* | (2006.01) | |
| *C07C 229/00* | (2006.01) | |
| *C08G 65/22* | (2006.01) | |
| *C08L 71/02* | (2006.01) | |
| *A61K 8/86* | (2006.01) | |
| *C08G 65/332* | (2006.01) | |
| *C08G 65/333* | (2006.01) | |

(52) U.S. Cl.
CPC . *A61K 8/86* (2013.01); *A61Q 17/04* (2013.01); *C08G 2261/122* (2013.01); *C08L 2205/05* (2013.01); *C08G 65/22* (2013.01); *C08L 71/02* (2013.01); *C08G 65/3326* (2013.01); *C08G 65/3331* (2013.01); *C08G 2650/24* (2013.01)
USPC .............................. 424/60; 424/70.9; 560/50

(58) Field of Classification Search
None
See application file for complete search history.

(56) References Cited

U.S. PATENT DOCUMENTS

| | | |
|---|---|---|
| 2007/0092459 A1 | 4/2007 | Bleckmann et al. |
| 2007/0172437 A1 | 7/2007 | Bertz et al. |

FOREIGN PATENT DOCUMENTS

| | | |
|---|---|---|
| WO | WO 2005/092282 | 10/2005 |
| WO | WO 2005092282 A1 * | 10/2005 |

OTHER PUBLICATIONS

Sunder (Hyperbranched Polyether-Polyols Based on Polyglycerol: Polarity Design by Block Copolymerization with Propylene Oxide, 33 Macromolecules 309-14 (2000).*
International Search Report and Written Opinion for PCT/EP2010/069181, mailed Oct. 7, 2011.

* cited by examiner

*Primary Examiner* — H. Sarah Park
(74) *Attorney, Agent, or Firm* — Nixon & Vanderhye P.C.

(57) ABSTRACT

The invention relates to novel polyglycerol based UV-filters as well as to topical compositions comprising such novel polyglycerol based UV-filters. Furthermore, the invention relates to the use of such novel polyglycerol based UV-filters to enhance the solubility of butyl methoxydibenzoylmethane or bis-ethylhexyloxyphenol methoxyphenyl triazine in cosmetic oils.

5 Claims, No Drawings

COMPOUND

This application is the U.S. national phase of International Application No. PCT/EP2010/069181, filed 8 Dec. 2010, which designated the U.S. and claims priority to EP Application No. 09178503.0, filed 9 Dec. 2009, the entire contents of each of which are hereby incorporated by reference.

The invention relates to novel polyglycerol based UV-filters as well as to topical compositions comprising such novel polyglycerol based UV-filters. Furthermore, the invention relates to the use of such novel polyglycerol based UV-filters to enhance the solubility of butyl methoxydibenzoylmethane or bis-ethylhexyloxyphenol methoxyphenyl triazine in cosmetic oils.

Sun care products have evolved considerably over the years. Earlier formulations were intended to protect the user from UV-B radiation (UVB) as was once thought that UV-B rays were the most important contributors to wrinkling, skin disease, and skin cancer. However, more recent studies have shown that UV-A radiation (UVA) is equally or even more important in the development of solar damage and skin diseases, such as lupus erythematosus and melanoma and non-melanoma skin cancers. Thus, today's focus is toward eliminating as much of UVA (320-400 nm) and/or UVB (280-320 nm) light as possible. This is reflected by novel regulations (EU recommendation 2005, FDA monograph 2008) which require the UVA protection to be at least one third of the UVB protection provided by the sun-care product.

Due to the increasing demand for high SPF sun care products with a UVA protection complying with the above mentioned regulations, more UV-filter substances at elevated levels have to be incorporated into the sun care products;

In order to achieve the UVA protection required by the novel regulations today's sun-care products often contain butyl methoxydibenzoylmethane (BMDBM, e.g. sold as Parsol® 1789), the only globally approved UVA screening agent.

BMDBM, however, exhibits only a limited solubility in the conventional cosmetic oils used for the solubilisation of solid UV-filter substances in order to enable their incorporation into cosmetic preparations (such as e.g. the cosmetic oils $C_{12-15}$ alkyl benzoate or diisopropyl sebaceate), which is typically less than 20%. As a consequence sun-care products containing high amounts BMDBM require high amounts of such cosmetic oils in order to solubilize BMDBM and avoid a re-crystallization in the product, which in turn, however, often results in an unpleasant oily gritty and/or tacky skin feel of the final products and a reduction in UV protection performance.

Thus, there is an ongoing need to reduce the amount of cosmetic oils used in sun care products. In particular, there is a need for agents which are capable to enhance the solubility of BMDBM in cosmetic oils and furthermore contribute itself to the SPF and/or UVA protection.

Surprisingly, it has been found that specific polyglycerol based UV filters are able to overcome the drawbacks of the prior art and in particular enhance the solubility of BMDBM in cosmetic oils conventionally used as solvents for BMDBM such as in particular $C_{12-15}$ alkyl benzoate or diisopropyl sebacate. Furthermore, the solubility of bis-ethylhexyloxyphenol methoxyphenyl triazine (BEMT, e.g. sold as Tinosorb® S) can also be significantly enhanced. These novel polyglycerol based UV filters thus allow the formulation of sun care products which are in line with the novel regulation while providing excellent sensorial properties such as e.g. in regard of skin feel and texture and an increased UV protection performance.

Thus, in one aspect the invention relates to novel polyglycerol based UV filters obtainable by a process comprising the steps of
 a.) ring-opening polymerization of x mol equivalents of glycidol using 1 mol equivalent of a polyol starter unit with y mol equivalents hydroxyl-groups followed by
 b.) block copolymerization with z×(x+y) mole equivalents of propylene oxide to form a hyperbranched polyether-polyol backbone carrying (x+y) mol equivalents hydroxyl-groups followed by
 c.) partial or total esterification of the hydroxyl groups with p-dimethylamino benzoic acid
  wherein x is an integer selected in the range from 3-16, y is an integer selected in the range from 1-6, and z is an integer selected in the range from 0-10.

Preferably, 15 to 100%, more preferably, 30-80%, most preferably about 60-75% of the hydroxyl groups of the hyperbranched polyether-polyol backbone are esterified with p-dimethylamino benzoic acid.

The amount of glycidol units x is in particular selected in the range of about 5 to 12, more in particular in the range of about 6 to 9 mol equivalents per mol equivalent of the polyol starter unit. Thus, in step a) x is in particular an integer selected in the range from 5 to 12, more in particular in the range from 6 to 9.

The amount of propylene oxide is preferably selected in the range from about 1 to 8, in particular in the range from about 1 to 2×(x+y). Thus, in step b) z is in particular an integer selected in the range from 1 to 8, more in particular in the range from 1 to 2.

If not all (i.e. 100%) hydroxyl groups of the hyperbranched polyether-polyol backbone are esterified with p-dimethylamino benzoic acid, residual hydroxyl groups may remain present in the polyglycerol based UV filters according to the invention. If desired, the residual hydroxyl groups can be reacted with suitable capping agents. Suitable capping agents include anhydrides or acid chlorides or acid esters of $C_1$ to $C_{20}$ linear or branched alkanoic acids such as e.g. acetanhydride, acetylchloride, 2-ethyl hexanoic acid (m)ethyl ester or 2-ethyl hexanoic acid chloride, 3,5,5-trimethylhexanoyl chloride or 3,5,5-trimethylhexanoyl (m)ethylester. The skilled person is aware of further suitable capping agents which can be used to introduce the corresponding capping groups. In all embodiments of the invention preferably the residual hydroxyl groups of the hyperbranched polyether-polyol backbone are capped with acetanhydride, acetyl chloride, 2-ethyl hexanoic acid chloride, 2-ethyl hexanoic acid (m)ethyl ester, 3,5,5-trimethylhexanoyl chloride or 3,5,5-trimethylhexanoyl (m)ethylester as well as mixtures thereof. Most preferably the capping groups are selected from 2-ethyl hexanoyl-, acetyl- and/or a 3,5,5-trimethylhexanoyl-groups.

In all embodiments of the invention preferably 30-80%, most preferably 60-75% of the hydroxyl groups of the hyperbranched polyether-polyol backbone are linked to a p-dimethylamino benzoyl moiety and the residual hydroxyl groups are linked to a capping group, in particular to an 2-ethylhexanoyl-, an acetyl- and/or a 3,5,5-trimethylhexanoyl group, in particular to an 2-ethylhexanoyl- or a 3,5,5-trimethylhexanoyl group.

Examples of polyol starter units include $C_{1-12}$-alkohols such as methanol or ethanol, glycidol, glycol, 1,4-cyclohexanedimethanol, hydroquinone bis(2-hydroxyethyl)ether, 2,2'-thiodiethanol, N-methyldiethanolamine, N-ethyldiethanolamine, 1,4-butanediol, 1,5-pentanediol, 1,6-hexanediol, 1,7-heptanediol, 1,8-octanediol, 1,9-nonanediol, 2-butene-1,4-diol, diethylene glycol, triethylene glycol, hexaethylene glycol, dipropylene glycol, polyethylene glycol, polypropylene glycol, tripentaerythritol, 1,2,6-hexanetriol, glycidol, 1,3,5-tris(2-hydroxyethyl)cyanuric acid, 1,3-bis[tris(hydroxymethyl)methylamino]propane, BIS-TRIS ['2,2-bis(hydroxyethyl)-(iminotris)-(hydroxymethyl)-methane], N,N,N',N'-tetrakis(2-hydroxyethyl)ethylenediamine, triethanolamine, diglycerol, glucose, fructose, sucrose, galactose, lactose, maltose, mannitol, dulcitol, threitol, sorbitol. In all embodiments of the invention the polyol starter unit is preferably selected from pentaerythritol, dipentaerythritol and/or trimethylolpropane, most preferably the polyol starter unit is trimethylolpropane.

The hyperbranched polyether-polyol backbone is obtainable by a one pot ring-opening polymerization reaction initiated by a polyol starter unit using glycidol as $AB_2$-type monomer i.e. building block followed by chain extension with propylene oxide to form the hyperbranched polyether-polyol backbone carrying free hydroxyl groups.

The theoretical amount of the free hydroxyl groups ((x+y) mol equivalents) in the hyperbranched polyether-polyol backbone can be calculated on the basis of the molar equivalents of hydroxyl groups per polyol starter unit (y) to the molar equivalents of glycidol building blocks used (x) as every glycidol unit adds one additional free hydroxyl group to the hyperbranched polyether-polyol backbone.

The term ring-opening polymerization refers to a form of addition polymerization, in which an initiator (i.e. a polyol starter unit) and/or the terminal end of a polymer acts as a reactive center where further cyclic monomeric building blocks, i.e. the glycidol join to form a larger polymer chain through ionic propagation. When the reactive center propagating chain is a cation the polymerization is called cationic ring-opening polymerization and when the active center is an anion the reaction is an anionic ring-opening polymerization. The ring-opening polymerization is performed using an effective amount of at least one catalyst, such as e.g. a base or an acid. Suitable catalysts are e.g. Lewis acids such as $AlCl_3$, $FeCl_3$, $SnCl_4$, and $BF_3$ and/or BrØnsted acids such as naphthalene sulphonic acid, para-toluene sulphonic acid, methane sulphonic acid, trifluoromethane sulphonic acid, trifluoroacetic acid, sulphuric acid and/or phosphoric acid, and/or onium salts, alcoholates such as e.g. potassium tert.-butylate or potassium methylate without being limited thereto. Further catalysts are alkali metals such as potassium or sodium, and alkali metal hydrides such as potassium hydride and sodium hydride.

In all embodiments of the invention preferably an anionic ring-opening polymerization using potassium hydride and/or potassium methylate as catalyst is used.

Further information on the preparation of the hyperbranched polyether-polyol backbone suitable for the subsequent coupling of p-dimethylamino benzoic acid are e.g. disclosed in Macromolecules 2000, 33, 309-314 which are enclosed herein by reference.

The esterification of the hydroxyl groups of the hyperbranched polyether-polyol backbone with p-dimethylamino benzoic acid can be performed by known method to a person skilled in the art, e.g. by transforming the acid into an acid chloride and subsequent reaction of the acid chloride with the hydroxyl groups of the hyperbranched polyether-polyol backbone in the presence of a base. An alternative method includes the transesterification using an ester of p-dimethylamino benzoic acid with the terminal hydroxyl groups of the hyperbranched polyether-polyol backbone in the presence of a base. Suitable esters are for example the methyl or the ethyl esters, in particular the methyl esters. Suitable bases according to the invention encompass carbonates such as potassium carbonate, alcoholates such as e.g. potassium tert.-butylate or potassium methylate, alkali metals such as potassium or sodium as well as alkali metal hydrides such as potassium hydride and sodium hydride as well as amines such as pyridine. In a preferred embodiment potassium tert.-butylate or pyridine is used. Preferably, in all embodiments of the invention the esterification is performed by transesterification of an ester of p-dimethylamino benzoic acid such as in particular p-dimethylamino benzoic acid (m)ethyl ester.

Preferably in all embodiments of the invention the polyglycerol based UV filters according to the invention have a number average molecular weight $M_n$ in the range of about 500 to 50,000 g mol$^{-1}$, more preferably of about 750 to 25,000 g mol$^{-1}$, most preferably of about 1,000 to 10,000 g mol$^{-1}$. The number average molecular weight Mn can be determined by Gel Permeation Chromatography (GPC) as described in the DIN 55672-1 using e.g. polystyrene standards.

The photostability of the polymer according to the present invention may be measured according to G. Berset et al. International Journal of Cosmetic Science 1996, 18(3), 167-177.

The polyglycerol based UV filters according to the present invention are useful to enhance the solubility of solid, oil soluble UV-filter substances such as BMDBM, bis-ethylhexyloxyphenol methoxyphenyl triazine, benzophenone-3, drometrizole trisiloxane, ethylhexyl triazone, diethylhexyl butamido triazone, 4-methyl benzylidene camphor or 2-(4-Diethylamino-2-hydroxy-benzoyl)-benzoic acid hexylester in cosmetic oils suitable as solvents for such solid, oil soluble UV-filter substances and suitable for the preparation of topical compositions such as in particular in $C_{12-15}$ alkyl benzoate or diisopropyl sebacate. In particular the polyglycerol based UV filters according to the present invention are useful to enhance the solubility of BMDBM or bis-ethylhexyloxyphenol methoxyphenyl triazine as well as mixtures thereof in cosmetic oils suitable as solvents for BMDBM or bis-ethylhexyloxyphenol methoxyphenyl triazine such as in particular in $C_{12-15}$ alkyl benzoate or diisopropyl sebacate.

Furthermore, the polyglycerol based UV filters according to the invention are useful as UV filter substances, i.e. for protecting ultraviolet-sensitive organic materials, in particular the skin and hair of humans and animals from the harmful effects of UV radiation. The polyglycerol based UV filters according to the present invention are not only suitable for "immediate protection from acute sun damage" such as sun burn (sun erythema), but also protect against damages through sunlight-induced oxidative stress and/or immune suppression and/or their consequences, i.e. photo aging. Furthermore, the polyglycerol based UV filters according to the present invention are also suitable to protect natural or artificial hair color. The polyglycerol based UV filters according to the present invention also lead to a synergistic UV-light absorption if used in combination with at least one further UV-filter substance. Furthermore, the polyglycerol based UV filters according to the present invention are suitable to reduce the stickiness e.g. of sand on the skin as well as to enhance the water resistance.

The polyglycerol based UV filters according to the present invention are colorless or yellowish, liquid, crystalline or semi-liquid substances. They are distinguished by high photostability, good solubility in organic solvents, especially cosmetic solvents such as in particular in $C_{12-15}$ alkyl benzoate (e.g., FINSOLV TN [Finetex Inc.]) or diisopropyl sebacate, and a short and economical synthetic route.

The present invention also relates to compositions, preferably to topical compositions comprising a polyglycerol based UV filter according to the present invention and a cosmetically or pharmaceutically acceptable carrier.

The amount of the polyglycerol based UV filter in the compositions according to the invention is not critical. Preferably an amount of at least 0.01 wt.-% is used. More preferably an amount of 0.5 to 20 wt.-%, in particular 1 to 10 wt.-% such as e.g. from about 2 to 5 wt.-% based on the total weight of the composition is incorporated into the compositions.

In a particular embodiment, the compositions according to the invention further comprise an additional amount of an oil soluble, solid UV-filter substance. Suitable oil soluble, solid UV-filter substances are in particular butyl methoxydibenzoylmethane (BMDBM), bis-ethylhexyloxyphenol methoxyphenyl triazine (BEMT, Tinosorb® S), benzophenone-3, drometrizole trisiloxane, ethylhexyl triazone, diethylhexyl butamido triazone, 4-methyl benzylidene camphor or 2-(4-Diethylamino-2-hydroxy-benzoyl)-benzoic acid hexylester as well as mixtures thereof.

In a particular embodiment, the topical composition according to the invention comprises BMDBM as oil soluble, solid UV-filter substance in an amount of at least 0.01 wt.-%. Particularly, the topical composition comprises BMDBM in an amount of 0.5 to 5 wt.-%, most in particular in an amount of 2 to 5 wt.-% based on the total weight of the composition.

In a further particular embodiment, the topical composition according to the invention further comprises bis-ethylhexyloxyphenol methoxyphenyl triazine in an amount of at least 0.01 wt.-%. Particularly, the topical composition comprises bis-ethylhexyloxyphenol methoxyphenyl triazine in an amount of 0.5 to 5 wt.-%, most in particular in an amount of 1 to 3 wt.-% based on the total weight of the composition.

It is also particularly advantageous if the topical composition according to the present invention comprises as solid UV absorbers BMDBM and bis-ethylhexyloxyphenol methoxyphenyl triazine in the amounts given above. Particularly BMDBM is incorporated in an amount of 2 to 5 wt.-% and bis-ethylhexyloxyphenol methoxyphenyl triazine in an amount of 1 to 3 wt.-% based on the total weight of the composition.

Where convenient other conventional UV-filter substances may be added into the topical compositions of the invention. The combination of UV-filter substances may show a synergistic effect. These additional UV-filter substances are advantageously selected from among acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4,2,2', 4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as polysilicone-15 (PARSOL® SLX); drometrizole trisiloxane (Mexoryl® XL); imidazole derivatives such as e.g. 2-phenyl benzimidazole sulfonic acid and its salts (PARSOL® HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like; salicylate derivatives such as isopropylbenzyl salicylate, benzyl salicylate, butyl salicylate, ethylhexyl salicylate PARSOL® EHS, Neo Heliopan® OS), isooctyl salicylate or homomethyl salicylate (homosalate, PARSOL® HMS, Neo Heliopan® HMS) and the like; triazine derivatives such as ethylhexyl triazone (Uvinul® T-150), diethylhexyl butamido triazone ethylhexyl triazone (Uvinul® T-150), diethylhexyl butamido triazone (Uvasorb® HEB), 2,4,6-Tris-(biphenyl)1,3,5-triazine and the like, merocyanines as e.g. disclosed in DE10 2007 024 345 on page 4, paragraph 19 which are incorporated by reference herein, encapsulated UV-filters such as encapsulated ethylhexyl methoxycinnamate (Eusolex® UV-pearls) or microcapsules loaded with UV-filters as e.g. disclosed in EP 1471995 and the like; dibenzoylmethane derivatives such as 4-tert.-butyl-4'-methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3,-tetramethyl-butyl)-phenol (Tinosorb® M) and the like; bis-ethylhexyloxyphenol methoxyphenyl triazine (Tinosorb® S) and the like; phenylene-1,4-bis-benzimidazolsulfonic acids or salts such as 2,2-(1,4-phenylene)bis-(1H-benzimidazol-4,6-disulfonic acid) (Neo Heliopan® AP); amino substituted hydroxybenzophenones such as 2-(4-Diethylamino-2-hydroxy-benzoyl)-benzoic acid hexylester (Uvinul® A plus) or 1,1'-(1,4-piperazinediyl)bis[1-[2-[4-(diethylamino)-2-hydroxybenzoyl]phenyl]-methanone (CAS No 919803-06-8); Ionic UV-A filters as described in the International Patent Publication WO2005080341 A1; pigments such as microparticulated ZnO or TiO$_2$ and the like. The term "microparticulated" refers to a particle size from about 5 nm to about 200 nm, particularly from about 15 nm to about 100 nm. The pigments may also be coated by other metal oxides such as e.g. aluminum or zirconium oxides or by organic coatings such as e.g. polyols, methicone, aluminum stearate, alkyl silane. Such coatings are well known in the art. Furthermore, the pigments (ZnO, TiO$_2$) can be used in the form of commercially available oily or aqueous pre-dispersions. These pre-dispersions may further contain a dispersing aid and/or solubilisator.

Particularly preferred additional UV-filter substances to be used in combination with a polyglycerol based UV filter according to the present invention are the commercially available and widely used UV-filter substances octocrylene (PARSOL® 340), 4-methyl benzylidene camphor (PARSOL® 5000), ethylhexyl methoxycinnamate (PARSOL® MCX), ethylhexyl triazone (Uvinul® T-150), diethylhexyl butamido triazone (Uvasorb® HEB), 2,2'-methylene-bis-(6-(2H-benzotriazole-2-yl)-4-(1,1,3,3,-tetramethylbutyl)-phenol (Tinosorb® M), bis-ethylhexyloxyphenol methoxyphenyl triazine (Tinosorb® S), 2,2-(1,4-phenylene)bis-(1H-benzimidazol-4,6-disulfonic acid (NeoHeliopan® AP), 2-(4-Diethylamino-2-hydroxy-benzoyl)-benzoic acid hexylester (Uvinul® A plus), 1,1'-(1,4-piperazinediyl)bis[1-[2-[4-(diethylamino)-2-hydroxybenzoyl]phenyl]-methanone (CAS No 919803-06-8), polysilicone-15 (PARSOL® SLX), 2-phenyl benzimidazole sulfonic acid (PARSOL® HS), ethylhexyl salicylate (PARSOL® EHS), homomethyl salicylate (PAR- SOL® HMS), Benzophenone-3 (Uvinul® M 40), Benzophenone-4 (Uvinul® MS 40), microfine titanium dioxide such as in particular PARSOL® TX as well as mixtures thereof.

The additional UV-filter substances are generally present in the compositions according to the invention in proportions ranging from 0.1 to 30 wt.-%, preferably ranging from 0.2 to 15 wt.-%, most preferably ranging from 0.5 to 10 wt.-% with respect to the total weight of the composition.

As dibenzoylmethane derivatives in particular BMDBM have a limited photostability it may be desirable to photostabilize these UV-filter substances in the topical compositions according to the invention. Thus, the invention also relates to topical compositions according to the invention which next to a dibenzoylmethane derivative such as in particular BMDBM also contain an effective amount of a stabilizer. The term effective amount of a stabilizer refers to an amount suitable for the photostabilization of a dibenzoylmethane derivative. The amount may vary from stabilizer to stabilizer (e.g. based on the mode of action) and can easily been determined by a person skilled in the art with normal trials, or with the usual considerations regarding the formulation of cosmetic composition. Suitable amounts may range from 0.01 to 1 wt.-% as well as from 0.5 to 20 wt.-%, such as 1 to 10 wt.-% with respect to the total weight of the composition.

Suitable stabilizers include octocrylene, diethylhexyl-2,6-naphthalate, polyester-8, diethylhexyl syringylidenemalonat, butyloctyl salicylate, polysilicone-15, tris(tetramethylhydroxypiperidinol)citrate, benzotriazolyl dodecyl p-cresol, benzophenone-3,4-methylbenzylidene camphor, Methoxycrylene (Solastay S1) and/or bis ethylhexyloxyphenol methoxyphenyl triazine. Particularly suitable as stabilizer is octocrylene.

Thus, in a further embodiment, the invention also relates to a topical composition comprising a polyglycerol based UV filter according to the invention, BMDBM and octocrylene or Methoxycrylene, in particular octocrylene, preferably the polyglycerol based UV filter is used in an amount of 0.5 to 20 wt.-%, BMDBM in an amount of 2 to 5 wt.-% and octocrylene in an amount of 2 to 10 wt.-%.

In another particular embodiment the topical compositions according to the present invention are free of p-methylbenzylidene camphor.

Preferably, the topical compositions according to the present invention furthermore contain one or more preservatives such as e.g. Methylparabene, Ethylparabene, Propylparabene or Butylparabene, Isobutylparabene, Benzoic Acid and its salts (e.g. Sodium Benzoate), Sorbic Acid and its salts (e.g. Potassium Sorbate, Dehydracetic Acid and its salts, Bronopol, Triclosan, Imidazolidinyl Urea, Phenoxyethanol, Benzyl Alcohol, Methylchloroisothiazolinone, Methylisothiazolinone, Chlorphenesin, Ethylhexylglycerin, Iodopropinylbutylcarbamate or Pentylene Glycol as well as mixtures thereof and without being limited thereto. A total content of about 0.01 to 2 wt.-%, such as in particular 0.05 to 1 wt.-% of preservatives with respect to the total weight of the composition is preferred.

The topical compositions according to the present invention may in particular contain further ingredients such as moisturizers; anti-oxidants; insect repellents; ingredients for skin lightening, tanning prevention and/or treatment of hyperpigmentation; tanning agents, ingredients for preventing or reducing wrinkles, lines, atrophy and/or inflammation; as well as topical anesthetics.

Particularly suitable moisturizers for the incorporation into the topical compositions according to the invention are glycerin, lactic acid and/or lactates, in particular sodium lactate, butylene glycol, propylene glycol, biosaccaride gum-1, glycine soja, ethylhexyloxyglycerin, pyrrolidoncarboxy acid, hydroxyethylurea and urea. It is further advantageous to use polymeric moisturizer such as water soluble or water gelifiable polysaccharides. In particular advantageous are e.g. hyaluronic acid, chitosan and/or a polysaccharid rich in fucose [CAS No 178463-23-5, commercially available as Fucogel® 1000 by SOLABIA S.A.]. The moisturizers can also be used as anti-ageing ingredients such as e.g. for the treatment of photo-aged skin.

The topical compositions according to the invention preferably contain at least one moisturizer in an amount (in total) of 0.1 to 20 wt.-%, preferably 0.5 to 10 wt.-% based on the total weight of the composition.

Particularly suited antioxidants for the topical compositions according to the invention encompass vitamin E and its derivatives such as particularly tocopheryl acetate. Tocopheryl acetate may be present in the topical compositions in an amount from about 0.05 wt.-% to about 25 wt.-%, in particular 0.05 wt.-% to 5 wt.-%. Another vitamin E derivative of interest is tocopheryl linoleate. Tocopheryl linoleate may be present in the topical composition in an amount from about 0.05 wt.-% to about 25 wt.-% in particular 0.05 wt.-% to 5 wt.-%.

Another suitable antioxidant is vitamin A and/or its derivatives. In particular retinoid derivatives such as retinyl palmitate or retinyl propionate is used in the topical compositions according to the invention in an amount of 0.01-5 wt.-%, in particular 0.01-0.3 wt.-%. The vitamin A and/or its derivatives can also be used in an encapsulated form.

Another suitable antioxidant is Vitamin C (ascorbic acid) and/or its derivatives. In particular ascorbyl phosphate such as Stay C (sodium ascorbyl monophosphate) is used in the topical compositions according to the invention in an amount of 0.1-5 wt.-% in particular 0.1-2 wt.-%.

Suitable insect repellents include N,N-Diethyl-3-methylbenzamid (Meta-delphene, "DEET"), Dimethylphtalat (Palatinol M, DMP), 1-Piperidincarbonsäure-2-(2-hydroxyethyl)-1-methylpropylester as well as particularly 3-(N-n-Butyl-N-acetyl-amino)-propionic acid (available as Insect Repellent® 3535 at Merck) as well as mixtures thereof.

Suitable skin lightening (depigmentation) agents to be used in the topical compositions according to the invention encompass alpha-arbutin, resveratrol, hydroquinone, azelaic acid, kojic acid as well as ascorbyl phosphates such as Magnesium-L-ascorbyl-2-phosphate (MAP) or sodium ascorbyl monophosphate.

Suitable tanning agents are dihydroxyacetone, erythrulose and/or melanine derivates in an amount of 1 to 10 wt.-% based on the total weight of the composition according to the invention.

Further examples of cosmetically active ingredients suitable to be used in the topical composition according to the invention comprise peptides (e.g., Matrixyl™ [pentapeptide derivative]), oligopeptides, wax-based synthetic peptides (e.g., octyl palmitate and tribehenin and sorbitan isostearate and palmitoyl-oligopeptide), glycerol, alpha-glycosylrutin, natural or synthetic flavanoids or isoflavanoids, creatine, creatinine, guanidine (e.g. amino guanidine); vitamins and derivatives thereof such as vitamin C (ascorbic acid), vitamin A (e.g., retinoid derivatives such as retinyl palmitate or retinyl propionate), vitamin E (e.g., tocopherol acetate), vitamin $B_3$ (e.g. niacinamide) and vitamin $B_5$ (e.g. panthenol), vitamin $B_6$ and vitamin $B_{12}$, biotin, folic acid; anti-acne actives or medicaments (e.g. resorcinol, salicylic acid, and the like); antioxidants (e.g. phytosterols, lipoic acid); flavonoids (e.g. isoflavones, phytoestrogens); skin soothing and healing agents such as aloe vera extract, allantoin and the like; agents suitable for aesthetic purposes such as essential oils, fragrances, skin sensates, opacifiers, aromatic compounds (e.g., clove oil, menthol, camphor, eucalyptus oil, and eugenol), desquamatory actives, hydroxy acids such as AHA acids, poly unsaturated fatty acids, radical scavengers, farnesol, antifungal actives in particular bisabolol, alkyldiols such as 1,2-pentanediol, hexanediol or 1,2-octanediol, phytol, polyols such as phytanetriol, ceramides and pseudoceramides, amino acids, protein hydrolysates, polyunsaturated fatty acids, plant extracts like kinetin, DNA or RNA and their fragmentation products, carbohydrates, conjugated fatty acids, carnitin, carnosine, biochinonen, phytofluen, phytoen, and their corresponding derivatives and co-enzyme Q10 (ubiquinone) without being limited thereto.

The additional cosmetically active ingredient is typically included in an amount of at least 0.001 wt. % based on the total weight of the topical composition. Generally, an amount of about 0.001 wt. % to about 30 wt. %, preferably from about 0.001 wt. % to about 10 wt. % of an additional cosmetically active agent is used.

Particularly preferred examples of ingredients to be used in the compositions according to the invention are vitamin C (ascorbic acid) and/or its derivatives (e.g. ascorbyl phosphate such as Stay C (sodium ascorbyl monophosphate) from DSM Nutritional Products Ltd.), vitamin A and/or its derivatives (e.g., retinoid derivatives such as retinyl palmitate or retinyl propionate), vitamin E and/or its derivatives (e.g., tocopherol acetate), vitamin $B_6$, vitamin $B_{12}$, biotin and/or co-enzyme Q10.

The topical cosmetic compositions of the invention can also contain usual cosmetic or pharmaceutical adjuvants and additives, such as preservatives, film forming agents, antioxidants, fatty substances/oils and/or waxes, water, organic solvents, silicones, thickeners, softeners, emulsifiers, antifoaming agents, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, perfumes or any other ingredients usually formulated into cosmetic compositions such as alcohols, polyols or electrolytes. Such cosmetic ingredients commonly used in the skin care industry, which are suitable for use in the compositions of the present invention are e.g. described in the CTFA Cosmetic Ingredient Handbook, Second Edition (1992) without being limited thereto.

The necessary amounts of the cosmetic and pharmaceutical adjuvants and additives can—based on the desired product form—easily be chosen by a skilled person in this field and will be illustrated in the examples, without being limited hereto.

The usual cosmetic adjuvants and additives such as e.g. emulsifiers, thickeners, surface active ingredients and film formers can show synergistic effects which can be determined by the expert in the field with normal trials, or with the usual considerations regarding the formulation of cosmetic composition.

The fatty substances can be an oil or a wax, or mixtures thereof. By the term "oil" is intended a compound which is liquid at ambient temperature. By the term "wax" is intended a compound which is solid or substantially solid at ambient temperature and for which the melting point is generally greater than 35° C.

Exemplary oils are mineral oils (liquid paraffin); vegetable oils (sweet almond, macadamia, blackcurrant seed or jojoba oil); synthetic oils, such as perhydrosqualene, fatty alcohols, acids or esters (such as the $C_{12-15}$ alkyl benzoate marketed under the trademark "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; polyalkylenes and their mixtures.

Preferably the oils used in the compositions according to the invention are selected from the list of polar oils such as the lecitines and fatty acid triglycerides, namely triglycerinester of saturated or unsaturated, branched or linear alkanoic acids with a chain length of 8 to 24, particularly 12 to 18C-atoms. The fatty acid triglycerides may preferably be selected from the group of synthetic, semi synthetic and natural oils such as e.g. cocoglyceride, olive oil, sunflower oil, soy bean oil, peanut oil, palm oil, sweet almond oil macadamia oil, coconut oil etc.

Further particularly suitable are natural waxes such as bees wax, shea butter, and/or lanolin.

Further particularly suitable polar oils according to the present invention may be selected from the group of esters of saturated or unsaturated, branched or linear alkanoic acids with a chain length of 3 to 30 C-atoms and saturated or unsaturated, branched or linear alcohols with a chain length of 3 to 30C-atoms as well as from the group of esters from aromatic carbonic acids and saturated or unsaturated, branched or linear alcohols with a chain length of 3 to 30C-atoms. Such ester oils are particularly selected from the group of phenylethylbenzoate, octylpalmitate, octylcocoate, octylisostearate, octyldodeceylmyristate, octyldodecanol, cetearylisononanoate, isopropylmyristate, isopropylpalmitate, isopropylstearate, isopropyloleate, n-butylstearate, n-hexyllaurate, n-decyloleate, isooctylstearate, isononylstearate, isononylisononanoate, 2-ethylhexylpalmitate, 2-ethylhexyllaurate, 2-hexyldecylstearate, 2-octyldodecylpalmitate, stearylheptanoate, isopropyl lauroyl sarkosinate, oleyloleate, oleylerucate, erucyloleate, erucylerucate, tridecylstearate, tridecyltrimellitate as well as synthetic and semi synthetic and natural mixtures of such esters such as e.g. jojoba oil.

Further particularly suitable oils may be selected from the group of dialkyl ether and dialkylcarbonates such as particularly dicaprylylether (Cetiol OE) and/or dicaprylylcarbonate, (e.g. available as Cetiol CC at Cognis).

Further particularly suitable oils may be selected from the group of isoeikosan, neopentylglykoldiheptanoate, propylenglykoldicaprylaet caprylate/dicaprate, caprylic/capric/diglyceryl succinate, butylene glyckol dicaprylate/dicaprate, $C_{12-13}$-Alkyllactate, Di-$C_{12-13}$-alkyltartrate, triisostearin, dipentaerythrityl hexacaprylate hexacaprate, propylenglykolmonoisostearate, tricaprylin and dimethylisosorbid.

It is particularly advantageous if the oil phase of the topical compositions according to the invention contains an amount of $C_{12-15}$-alkylbenzoate or consists essentially thereof.

Further particularly suitable oily components are e.g. butyloctylsalicylate (e.g. Hallbrite BHB from CP Hall), hexadecylbenzoate and butyloctylbenzoate as well as mixtures thereof (e.g. Hallstar AB).

The topical compositions according to the present invention may also contain apolar oils such as e.g. branched or linear hydrocarbons and waxes, in particular mineral oil, vaseline (Petrolatum), paraffin oil, squalan and squalen, polyolefins, hydrogenated polyisobutenes, $C_{13-16}$ isoparaffin and isohexadecan. Within the group of polyolefins polydecenes are preferred.

Exemplary waxy compounds in particular suitable for the use in the compositions according to the invention are paraffin wax, carnauba wax, beeswax or hydrogenated castor oil.

Exemplary organic solvents in particular suitable for the use in the compositions according to the invention include the lower alcohols and polyols having at most 8 carbon atoms. In particular the compositions according to the invention comprise ethanol in an amount of 5 to 40 wt.-% based on the total weight of the composition.

The thickeners are advantageously selected, in particular, from among the cross linked polyacrylic acids or modified or unmodified guar gums and celluloses, such as hydroxypropylated guar gum, methylhydroxyethylcellulose and hydroxypropylmethylcellulose.

Suitable film forming agents include polymers in the basis of PVP such as in particular copolymers of polyvinylpyrrolidon e.g. PVP hexadecen copolymer and PVP eicosen copolymer which are available as Antaron V216 and Antaron V220 at GAF Chemicals corporations. Further suitable film forming agents include polymeric film formers such as sodiumpolystyrenesulfonate (e.g. Flexan 130 from National Starch and Chemical Corp.) and/or polyisobuten (e.g. Rewopal PIB1000 from Rewo). Further suitable polymers are e.g. polyacrylamide (Seppigel 305), polyvinylalkohole, PVP, PVP/VA copolymers, polyglycols and acrylate/octylacralymid copolymers (e.g. Dermacryl 79). Further suitable is the use of hydrated castor oil dimerdilinoleat (CAS 646054-62-8, INCI Hydrogenated Castor Oil Dimer Dilinoleate), or PPG-3 Benzylethermyristate (CAS 403517-45-3).

The topical compositions according to the invention may further comprise one or several compounds from the group of siloxanes elastomers listed in order to enhance the water resistance and/or enhance the light protection factor such as in particular siloxanes elastomers in the form of spherical powders with the INCI nomenclature Dimethicone/Vinyl Dimethicone Crosspolymer, such as e.g. DOW CORNING 9506 Powder (by Dow corning).

It is particularly advantageous if the siloxane elastomer is used in combination with hydrocarbon oils, synthetic oils, synthetic esters, synthetic ether or mixtures thereof.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The term "topical composition" as used herein refers in particular to a cosmetic composition that can be topically applied to mammalian keratinous tissue, particularly human skin and hair.

The term "cosmetic preparation" or "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Preparations", Verlag für chemische Industrie (ed. H. Ziolkowsky), 4$^{th}$ edition, 1992.

Preferred topical compositions according to the invention are skin care preparations, hair care preparations, decorative preparations, and functional preparations.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples for care preparations are hair-washing preparations in the form of shampoos, hair conditioners, hair-care preparations such as e.g. pretreatment preparations, hair tonics, styling creams, gels such as styling gels, pomades, hair rinses, treatment packs, intensive hair treatments, hair-straightening preparations, liquid hair-setting preparations, hair foams (hair mousses) and hairsprays.

Examples of decorative preparations are, in particular, lipsticks, eye shadows, massacres, dry and moist make-up formulations, rouges and/or powders.

Examples of functional preparations are cosmetic or pharmaceutical compositions containing active ingredients such as hormone preparations, vitamin preparations, vegetable extract preparations, anti-ageing preparations, and/or antimicrobial (antibacterial or antifungal) preparations without being limited thereto.

In a particular embodiment the topical compositions according to the invention are light-protective preparations, such as sun protection milks, sun protection lotions, sun protection creams, sun protection oils, sun blocks or tropical's or day care creams with a SPF (sun protection factor). Of particular interest are sun protection creams, sun protection lotions, sun protection milks and sun protection preparations in the form of a spray or aerosol.

In another particular embodiment the topical compositions are hair-washing preparations in the form of shampoos or hair treatment preparations intended to be left in the hair (and not washed out) such as hair-setting preparations, hairsprays, gels, pomades, styling creams or hair foams (hair mousses), particularly hairsprays, gels or hair foams (hair mousses).

A shampoo may, for example, have the following composition: from 0.01 to 5 wt.-% of a polyglycerol based UV filter according to the present invention, 12.0 wt.-% of sodium laureth-2-sulfate, 4.0 wt.-% of cocamidopropyl betaine, 3.0 wt.-% of sodium chloride, and water ad 100 wt.-%.

The topical compositions according to the present invention may be in the form of a suspension or dispersion in solvents or fatty substances, or alternatively in the form of an emulsion or micro emulsion (in particular of O/W- or W/O-type, Si/W- or W/Si-type), PIT-emulsion, multiple emulsion (e.g. O/W/O- or W/O/W-type), pickering emulsion, hydrogel, alcoholic gel, lipogel, one- or multiphase solution or vesicular dispersion or other usual forms, which can also be applied by pens, as masks or as sprays. Preferably, the topical compositions are in the form of an emulsion or dispersion.

In one particular embodiment, the topical compositions according to the invention are in the form of an O/W emulsion. If the topical composition according to the invention is an O/W emulsion, then it contains advantageously at least one O/W- or Si/W-emulsifier selected from the list of glycerylstearatcitrate, glycerylstearate (self emulsifying), stearic acid, salts of stearic acid, polyglyceryl-3-methylglycosedistearate, ceteareth-20, steareth-2, steareth-12, PEG-40 stearate, Further suitable emulsifiers are phosphate esters and the salts thereof such as cetyl phosphate (Amphisol® A), diethanolamine cetyl phosphate (Amphisol®DEA), potassium cetyl phosphate (Amphisol® K), sodiumcetearylsulfat, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Lauryl Glucoside, Decyl Glucoside, Sodium Stearoyl Glutamate, Sucrose Polystearate and Hydrated Polyisobuten. Furthermore, one or more synthetic polymers may be used as an emulsifier. For example PVP eicosene copolymer, acrylates/$C_{10-30}$alkyl acrylate crosspolymer, acrylates/steareth-20 methacrylate copolymer, PEG-22/dodecyl glycol copolymer, PEG-45/dodecyl glycol copolymer, and mixtures thereof. The at least one O/W emulsifier is preferably used in an amount of about 0.001 to 10 wt.-%, more preferably in an amount of 0.1 to 7 wt.-% with respect to the total weight of the composition. Additionally the topical composition contains advantageously at least one co-emulsifier selected from the list of alkyl alcohols such as Cetyl Alcohol (Lorol C16, Lanette 16) Cetearyl Alcohol (Lanette O), Stearyl Alcohol (Lanette 18), Behenyl Alcohol (Lanette 22), Glyceryl Monostearate, Glyceryl Myristate (Estol 3650), Hydrogenated Coco-Glycerides (Lipocire Na10) without being limited to this and mixtures thereof.

In another particular embodiment, the topical compositions according to the invention are W/O emulsions. If the topical composition according to the invention is a W/O emulsion, then it contains advantageously at least one W/O— or W/Si-emulsifier selected from the list of polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone.

The at least one W/O emulsifier is preferably used in an amount of about 0.001 to 10 wt.-%, more preferably in an amount of 0.2 to 7 wt.-% with respect to the total weight of the composition.

The topical compositions according to the invention particularly exhibit a pH in the range of 3-10, preferably in the range of pH of 5-8, most preferred in the range of pH 4-6 which can be adjusted with conventional acids, bases or buffering solutions.

Which amount of the topical composition has to be applied, depends on the concentration of the active ingredient(s) in the product and the desired cosmetic effect(s). A typical "leave-on" composition like a skin care emulsion or light-protective preparation, for example, is usually applied in an amount of about 0.5 to about 2 mg per $cm^2$ skin. The applied amount is normally not critical, and the desired effect(s) may be achieved by using more of the composition, repeating the application of the composition and/or applying a composition which contains more of the active ingredient(s).

By "'leave-on' composition" as used herein a topical composition is meant which after having applied to the skin, is not removed intentionally. It is preferably left on the skin for a period of at least about 15 minutes, more preferably at least about 30 minutes, even more preferably at least about 1 hour, most preferably for at least several hours, e.g. up to about 12 hours.

The topical compositions according to the invention are in particular used for the protection against skin ageing (in particular photo ageing) and as sunscreen.

The following examples are provided to further illustrate the compounds and compositions of the present invention. These examples are illustrative only and are not intended to limit the scope of the invention in any way.

The names of the ingredients in the following tables are indicated as INCI names. All amounts are given as wt.-% based on the total weight of the composition.

| Gels | 1 | 2 | 3 | 4 | 5 | 6 | 7 | 8 |
|---|---|---|---|---|---|---|---|---|
| Acrylates/Octylacrylamide Copolymer | 1 | 1 | 1 | 1 | 1 | 1 | 1 | 1 |
| Alcohol Denat. | 50 | 62 | 59.2 | 52 | 56 | 59 | 51 | 54 |
| Butylene Glycol Dicaprylate/Dicaprate | | | 7.5 | | | 2 | 4 | |
| C12-15 Alkyl Benzoate | 5 | 8.5 | 5 | 2 | 7.5 | | 2 | 5 |
| Phenylethylbenzoate | 3 | | | 2.5 | | | 2.5 | |
| Cocoglyceride | | | | | | 2 | 5 | |
| Tridecylsalicylate | 2 | 1.5 | | | 3 | 1 | | 3 |
| Hydroxypropoylcellulose | 2 | 0.8 | 1 | 0.8 | 0.5 | 0.8 | 0.45 | 0.5 |
| Butyl Methoxydibenzoylmethane | 4.5 | 4.5 | | | 2.5 | 4.5 | | 3 |
| Merocyanine | | | | | 1.8 | | | 5 |
| 2,4,6-Tribiphenyl-4-yl-1,3,5 Triazine | | | 0.5 | 4 | | 6 | | |
| Diethylamino Hydroxybenzoyl Hexyl Benzoate | | | 4.5 | 3.5 | | | | |
| Ethylhexyl Methoxycinnamate | 5 | 9.5 | | 6.5 | 6.5 | 9.5 | | |
| Ethylhexyl Salicylate | 3 | 4.5 | 4.5 | 4.5 | | | | 5 |
| Homosalate | | | | | | 4.5 | | |
| Octocrylene | 8 | 4.8 | 9.5 | 4.3 | 3.8 | | | 4 |
| Ethylhexyl Triazone | | | | | 2 | | | |
| Benzophenone-3 | 3 | | | | | | | |
| Drometrizole Trisiloxane | | | | | 0.5 | 1 | | 1 |
| polyglycerol based UV filter according to the invention such as in particular the compound of example 1 or 2 | 8.0 | 1.5 | 2.5 | 5 | 3.5 | 1 | 20 | 15 |
| Bis-Ethylhexyloxyphenol Methoxyphenyltriazine | | | | | | 1 | | |
| Benzotriazoyl Dodecyl p-Cresol | | | | | | 8 | | |
| Butyloctyl Methoxycrylene | | | | | | | | 4 |
| Diethylhexyl Syringylidenemalonate | | 3.8 | | | | | | |
| Vitamin E Acetate | | | | | 0.5 | | 0.2 | 0.5 |
| Glycerin | 5 | | 3 | | | | | |
| Fragrance, colours | | | | | q.s | | | |
| Water | | | | | ad 100 | | | |

| Sprays | 1 | 2 | 3 | 4 | 5 | 6 | 7 | 8 | 9 | 10 | 11 | 12 |
|---|---|---|---|---|---|---|---|---|---|---|---|---|
| Acrylates/Octylacrylamide Copolymer | 1 | | | | 1 | 1 | | | 1 | | 1 | |
| VP/VA Copolymer | | 1 | | 0.5 | | | | 0.5 | | | | 0.5 |
| Alcohol Denat. | 42 | 57 | 60 | 53 | 35.5 | 43.5 | 40 | 53 | 35.5 | 20 | 34 | 53 |

| Sprays | 1 | 2 | 3 | 4 | 5 | 6 | 7 | 8 | 9 | 10 | 11 | 12 |
|---|---|---|---|---|---|---|---|---|---|---|---|---|
| Potassium Cetyl Phosphate | | | | | | | | | | 2 | 3 | |
| Cetearyl Alcohol | | | | | | | | | | 0.2 | | |
| Cetyl Alcohol | | | | | | | | | | | 0.3 | |
| Acrylates/C10-30 Alkyl Acrylate Crosspolymer | | | | | | | | | | 0.2 | 0.15 | |
| Cyclomethicone | 4.9 | 2 | 5 | 0.5 | 8 | 8 | 3 | 0.5 | 10 | 4 | 10 | 0.5 |
| Tridecylsalicylate | 0.5 | 2.5 | 4 | 7 | 10 | 3 | 3 | 7 | 4 | 0.5 | 4 | 7 |
| Bis-Ethylhexyloxyphenol Methoxyphenyltriazine | | | | | 1 | | | 1 | | | 1 | |
| Ethylhexyl Bis-Isopentylbenzoxazolyl phenyl Melamine | 0.5 | | 1 | | | 3 | | | | | | |
| Butyl Methoxy-dibenzoylmethane | 4.5 | 2 | | 3 | 5 | | | 3 | | 4 | 3 | 3 |
| Diethylamino Hydroxybenzoyl Hexyl Benzoate | | 2 | 3 | | | 4.5 | | | | | | |
| Ethylhexyl Methoxycinnamate | 9.5 | | | 7 | 6.5 | 8.5 | | 7 | | 7.5 | | 7 |
| Ethylhexyl Salicylate | 4.5 | 3.5 | 2 | 4 | 4.5 | 1.5 | | 4 | | | 4 | 4 |
| Drometrizole Trisiloxane | | 0.5 | | | | 1 | | | | 2 | | |
| 2,4,6-Tribiphenyl-4-yl-1,3,5 Triazine | 1 | | | 5 | | | 2 | | | | | 2 |
| Merocyanine | | | 3 | | | 0.5 | | | | 2 | | |
| Methylene Bis-Benztriazoyl Tetramethylbutylphenol | | | | | | | | 3 | | | | |
| 1,1'-(1,4-piperazinediyl)bis[1-[2-[4-(diethylamino)-2-hydroxybenzoyl] phenyl]-methanone | | | | | | | | | | | | 3 |
| Homosalate | 9.5 | 5 | 3 | | 9.5 | 5.5 | | | | 5 | | |
| Octocrylene | 9.5 | | 8 | | 7.5 | 8.5 | | | | 4 | 3 | |
| polyglycerol based UV filter according to the invention Vsuch as in particular the compound of example 1 or 2 | 0.5 | 2.5 | 6.8 | 1 | 2 | 4 | 20 | 10 | 25 | 15 | 20 | 10 |
| Butylene Glycol Dicaprylate/Dicaprate | | 9 | | | | | | | | 2 | | |
| $C_{12-15}$ Alkyl Benzoate | | 2 | | 2 | | | | 2 | 5 | | 5 | 2 |
| Phenylbenzoate | | | 7 | | 4 | | 7 | | 4 | | 4 | |
| Benzotriazoyl Dodecyl p-Cresol | | | | | | | | 3 | | | | 3 |
| Butyloctyl Methoxycrylene | | | | | | | | | | 4 | | |
| Diethylhexyl Syringylidenemalonate | | 2 | | | | | | | | | | |
| Diethylhexylnaphthalate | | 6 | | 3 | | | | 3 | | | | 3 |
| Isopropyl Lauroyl Sarcosinate | 2 | | 1 | | 3 | | 1 | | 3 | | 3 | |
| Phenyl Trimethicone | 2 | 5 | | | 1 | 2 | | | 1 | 2 | 1 | |
| Octyldodecanol | | | | 8 | | | | 8 | | | | 8 |
| Glycerin | 5 | 4 | 5 | 8 | 5 | 5 | 5 | 8 | 5 | 5 | 5 | 8 |
| Vitamine E Acetate | 0.1 | | 0.5 | | | | | 0.5 | | | | |
| Fragrance, Colours | | | | | | q.s | | | | | | |
| Water | | | | | | Ad 100 | | | | | | |

| O/W Emulsions | 1 | 2 | 3 | 4 | 5 | 6 | 7 | 8 | 9 | 3 |
|---|---|---|---|---|---|---|---|---|---|---|
| Glyceryl Stearate Citrate | 2 | 2 | 3 | | | | | | 3 | |
| Glyceryl Stearate SE | | | | 1 | 1 | 1.5 | | 1.5 | | |
| Cetearyl Alcohol + PEG-40 Rizinusoil + Sodium Cetearyl Sulfate | | | | 2.5 | 2.5 | 3 | | | | |
| Potassium Cetyl Phosphate | | | | | | | 2 | 2 | 1.5 | |
| Cetearyl Alcohol | | | 1 | 1 | | | 2 | 2 | 0.5 | 1 |
| Stearyl Alcohol | 0.5 | | | | | 2 | | | 0.5 | |
| Myristyl Myristate | 1 | 1 | | | 3 | | | 2 | | |
| Acrylates/$C_{10-30}$ Alkyl Acrylate Crosspolymer | 0.1 | 0.2 | | | 0.1 | | | 0.2 | | |
| Carbomer | | 0.2 | 0.3 | 0.2 | | | | | | 0.3 |
| Xanthan Gum | 0.4 | | 0.2 | 0.2 | 0.3 | 0.4 | 0.2 | | 0.3 | 0.2 |
| $C_{12-15}$ Alkyl Benzoate | | 3 | | | 5 | | 4 | 5 | | |
| 2-Phenylethylbenzoate | 5 | 2 | | | | | | | | |
| Butylene Glycol Dicaprylate/Dicaprate | 5 | | | | 3 | 3 | | 7.5 | 3 | |
| Tridecylsalicylate | 1.5 | 2.5 | 0.25 | 5.9 | 7 | 15 | 5.9 | 7 | 6 | 0.25 |
| Dicaprylcaprate | 2 | 2 | | | 2 | 2 | | 2 | 2 | |
| Cyclomethicone | | | | 5 | 10 | | 5 | | | |
| Dimethicone | | | | | 5 | | | 5 | | |
| PVP Hexadecene Copolymer | | 0.5 | | | | 1 | 2 | | 1 | |
| Propylene Glycol | | | 1 | | 5 | 3 | | | 3 | 1 |
| Glycerin | 3 | 5 | 7 | 10 | 13 | 3 | 3 | 5 | 3 | 7 |
| Alcohol denat. | 2 | 3 | | 7 | | | | | | |
| Merocyanine | 1 | | | 3 | | 0.8 | | | | |
| Titanium Dioxide | 3 | | 2 | | 3 | | | | | |
| Phenylene-1,4-bis-(2-benzimidazyl)-3,3-5,5-tetrasulfonic Acid | 3 | 2 | | | | | | | | |
| Ethylhexyl Triazone | 2.5 | 2 | | 1 | | 1 | | | | |
| Phenylbenzimidazole Sulfonic Acid | | | 2 | | | 1 | 2 | | 1 | 2 |
| 4-Methoxycinnamate (2-ethylhexyl) ester | 9.5 | 5 | | 2 | | | | | | |
| Butyl Methoxydibenzoylmethane | 5 | 1 | | | 3 | | 4 | | | |
| Ethylhexylsalicylate | 5 | | 0.5 | 4 | 5 | | 4 | | 0.5 | |
| Polysilicone-15 | | | 4 | | | 1 | | | 4 | |
| Isoamyl p-Methoxycinnamate | | | 3 | 6 | | | | | | 6 |

-continued

| O/W Emulsions | 1 | 2 | 3 | 4 | 5 | 6 | 7 | 8 | 9 | 3 |
|---|---|---|---|---|---|---|---|---|---|---|
| Diethylamino Hydroxybenzoyl Hexyl Benzoate | | | | | | | | | 3 | |
| Methylene Bis-Benztriazoyl Tetramethylbutylphenol | | | 5 | | | | | | | |
| 1,1'-(1,4-piperazinediyl)bis[1-[2-[4-(diethylamino)-2-hydroxybenzoyl] phenyl]-methanone | | | | | | | | | | 5 |
| Ocotcrylene | 8 | | | | 5 | 7 | 4 | | 7 | |
| Bis-Ethylhexyloxyphenol Methoxyphenyltriazine | | 1 | | 1 | | 1 | 0.5 | | 1 | |
| polyglycerol based UV filter according to the invention such as in particular the compound of example 1 or 2 | 10 | 3 | 4 | 2 | 1 | 5 | 20 | 20 | 15 | 4 |
| Benzotriazoyl Dodecyl p-Cresol | | 0.9 | | | | | | | | |
| Butyloctyl Methoxycrylene | | | | | 3 | | | | | |
| Diethylhexyl Syringylidenemalonate | | | | | | | 2 | | | |
| Vitamine E Acetat | 0.2 | 0.2 | 0.2 | 0.3 | 0.1 | 0.5 | 0.3 | 0.1 | 0.5 | 0.2 |
| Disodium EDTA | 0.1 | 0.1 | 0.2 | 0.2 | 0.5 | 0.2 | 0.2 | 0.2 | 0.2 | 0.2 |
| Fragrance, Preservation agents | q.s | q.s | q.s | q.s | q.s | q.s | q.s | q.s | q.s | q.s |
| Colours, etc. | q.s | q.s | q.s | q.s | q.s | q.s | q.s | q.s | q.s | q.s |
| Citric Acid, Sodium Citrate | q.s | q.s | q.s | q.s | q.s | q.s | q.s | q.s | q.s | q.s |
| Sodium Hydroxide | q.s | q.s | q.s | q.s | q.s | q.s | | q.s | | q.s |
| Tromethamine | | | | | | | q.s | | q.s | |
| Water | | | | | ad 100 | | | | | |

| O/W Emulsions | 7 | 8 | 9 | 10 | 11 | 12 | 13 | 14 | 15 |
|---|---|---|---|---|---|---|---|---|---|
| Glyceryl Stearate | 2.5 | 2 | 1.2 | 1 | | | 1 | 1 | |
| PEG-40 Stearate | 1 | | | | | | | | |
| PEG-100 Stearate | | 2.5 | | | | | | 1 | |
| Ceteareth-20 | | | | | 1 | | | | |
| Glyceryl Stearate Citrate | | | | | | 0.5 | | | 0.5 |
| Potassium Cetyl Phosphate | | | | | | | 3 | 1.5 | 2 |
| Stearic Acid | | | 2.5 | 3 | | | | | |
| Cetearyl Alcohol | 4 | | | 2 | | | 2 | | |
| Stearyl Alcohol | | 2 | 1 | | | | | | |
| Cetyl Alcohol | | | 1 | 1 | | | | 0.5 | |
| Acrylates/C$_{10-30}$ Alkyl Acrylate Crosspolymer | | | | | 0.2 | 0.2 | 0.4 | 0.2 | 0.4 |
| Carbomer | 0.1 | | 0.2 | | | | | | |
| Xanthan Gum | | 0.3 | | | | | | 0.3 | |
| C$_{12-15}$ Alkyl Benzoate | 5 | | | 2 | 5 | 5 | 10 | 5 | 5 |
| Vaseline | 5 | | 3 | | | | | | |
| Butylene Glycol Dicaprylate/Dicaprate | | 4 | 2 | | 9 | | | 9 | |
| Hydrogenated Polydecene | | | 3 | | 2 | | | 2 | |
| Caprylic/Capric Triglyceride | 1 | 3 | | 5 | | 5 | 5 | | 5 |
| Cyclomethicone | | 5 | 2 | | | 10 | | | 10 |
| Methylpropandiol | 2 | | | | 3 | | | 3 | |
| Isopropyl Lauroyl Sarcosinate | | | | | | | | | |
| Glycerine | 7.5 | 10 | 4 | 5 | 5 | | 5 | 5 | |
| Alcohol denat. | 1 | 3 | 0.5 | 10 | 4 | 8 | | 4 | 8 |
| Butylene Glycol | | | 3 | | | | | | |
| Isotridecylsalicylate | | | 1 | 3 | 5 | 2 | 3 | 5 | |
| Titanium Dioxide | 1 | | 0.5 | 2 | | | | | 5 |
| Merocyanine | | | | | 1.8 | | | 5 | |
| 2,4,6-Tribiphenyl-4-yl-1,3,5 Triazine | | | 0.5 | 4 | | 6 | | | 6 |
| Ethylhexyl Bis-Isopentylbenzoxazolylphenyl Melamine | | 1 | | | 0.5 | | | 2 | |
| Ethylhexyl methoxycinnamate | 4 | | | | 2 | | | | |
| Phenylbenzimidazole Sulfonic Acid | 1.5 | | | 2 | | 2 | | | |
| Butyl Methoxydibenzoylmethane | 2.5 | | | 2 | | 3 | | 3 | |
| Methylbenzylidene Camphor | | | | | 2 | 3 | | | |
| Disodium Phenyl Dibenzimidazole Tetrasulfonic Acid | | | | | | | | | 2 |
| polyglycerol based UV filter according to the invention such as in particular the compound of example 1 or 2 | 1 | 2 | 4 | 0.75 | 5 | 2.5 | 25 | 20 | 16 |
| Ocotcrylene | | 5 | | | | 2 | | | 2 |
| Polysilicone-15 | | | | | 2 | 3 | | | |
| Ethylhexyl Salicylate | 3 | | | | 5 | | | 5 | |
| Homosalate | | | | 4 | | 2 | | 2 | 3 |
| Drometrizole Trisiloxane | 0.5 | | | 1 | | 2 | | | |
| Terephthalidene Dicamphor Sulfonic Acid | 0.75 | | | 0.5 | | 0.25 | | 1.5 | |
| Benzotriazoyl Dodecyl p-Cresol | 3 | | | | | | | | |
| Butyloctyl Methoxycrylene | | | | | | 2 | | | |
| Tapioca Starch | 1 | | 2.5 | | | 0.5 | | | 0.5 |
| Sodium Starch Octenylsuccinate | | | | | 1 | | 1 | | |
| Disodium EDTA | | 0.1 | | | | 0.5 | | | 0.5 |
| Fragrance, Preservatives | q.s | q.s | q.s | q.s | q.s | q.s | q.s | q.s | q.s |
| Sodium Hydroxide | q.s | q.s | q.s | q.s | q.s | q.s | q.s | q.s | q.s |
| Water | | | | | Ad 100 | | | | |

| W/O Emulsions | 1 | 2 | 3 | 4 | 5 | 6 | 7 | 8 | 9 | 10 | 11 | 1 | 3 | 5 |
|---|---|---|---|---|---|---|---|---|---|---|---|---|---|---|
| Polyglyceryl-2 Dipolyhydroxystearate | 3 | 5 | 3 | | | | | | 5 | 5 | 5 | 3 | 3 | |
| PEG-30 Dipolyhydroxystearate | | | 2 | 3 | 4 | 5 | 3 | 4 | | | | | 2 | 4 |
| Sodium Starch Octenylsuccinate | 0.5 | 0.4 | 0.6 | 0.3 | 0.5 | 1 | | 0.3 | 0.5 | 1 | 0.5 | 1 | 0.5 | 0.6 | 0.5 |
| Glycine | 0.3 | 0.3 | 0.5 | 0.4 | | | 0.4 | | | | | | 0.3 | 0.5 | |
| Alcohol denat. | 2 | 5 | 2 | 0.5 | 8 | 1 | | 8 | 5 | | | 3 | 2 | 2 | 8 |
| Magnesium Sulfate | 0.2 | 0.3 | 0.3 | 0.4 | 0.5 | 0.2 | 0.5 | 0.5 | 0.5 | 0.5 | 0.5 | 0.2 | 0.3 | 0.5 |
| C12-15 Alkyl Benzoate | 5 | 3 | | | 5 | | | 5 | | 4 | | 5 | | 5 |
| Triheptanoin | | 2 | | | | | | | | | | | | |
| Butyleneglycol Dicaprylat/Dicaprate | 5 | | | | 3 | 3 | | 3 | 3 | 6 | 3 | 5 | | 3 |
| Dicaprylyl Ether | | | | | 2 | | | 2 | | 2 | | | | 2 |
| Mineral Oil | | 4 | | 6 | | 8 | 6 | | 8 | | 8 | | | |
| Octyldodecanol | 2 | | | | | | | | | | | 2 | | |
| Dicapryl Caprate | | 2 | | | 2 | 2 | | 2 | 2 | 2 | 2 | | | 2 |
| Cyclomethicone | 5 | | 5 | 10 | | | | | | | | 5 | 5 | |
| Dimethicone | | | | 5 | | | 5 | | | | | | | |
| Isohexadecane | | 1 | | | | | | | | | | | | |
| Butylene Glycole | 5 | 8 | | | 3 | | | 3 | | | 3 | 5 | | |
| Glycerin | 3 | 5 | 7 | 10 | 3 | 3 | 10 | 3 | 3 | 3 | 3 | 3 | 7 | 3 |
| Tridecylsalicylate | | 1 | 2 | | | 0.5 | | | 0.5 | | 0.5 | | 2 | |
| 2-Phenylethylbenzoate | | | 2 | | 4 | | | 4 | | | | | 2 | 4 |
| Isopropyl Lauroyl Sarcosinate | | | 1 | | 2 | | | 2 | | | | | 1 | 2 |
| Ethylhexylmethoxycinnamate | 5 | | 7 | | 5 | | | 5 | | | | 5 | 7 | 5 |
| Ethylhexyl Triazone | 2 | 3 | 3 | | | 3 | | | | 1 | | 2 | 3 | |
| Ethylhexyl Bis-Isopentyl-benzoxazolylphenyl Melamine | | | | 3 | | | | 0.5 | | | | | | |
| Diethylhexyl Butamido Triazone | | 1.5 | 1.5 | | | 1.5 | | | | | | | 1.5 | |
| Butyl Methoxy dibenzoylmethane | | 4 | | | | | | | | 2 | 3 | | | |
| Methylbenzylidene Camphor | | | | | | | | | | | 2 | | | |
| 2,4,6-Tribiphenyl-4-yl-1,3,5 Triazine | | | 5 | | | | | 2 | | | | | 5 | |
| Merocyanine | | | | | 3 | | | | | 2 | | | | 3 |
| 2-(4-Diethylamino-2-hydroxybenzoyl)-Benzoic Acid Hexylester | | | | 2 | | | | 1 | | | | | | |
| polyglycerol based UV filter according to the invention such as in particular the compound of example 1 or 2 | 1 | 2 | 4 | 0.75 | 5 | 2.5 | 10 | 15 | 20 | 15 | 10 | 1 | 4 | 5 |
| Titanium Dioxide (Parsol TX) | 5 | 4 | 2 | | 3 | 4 | | 3 | | 3 | 4 | 5 | 2 | 3 |
| Polysilicone-15 | | | | | | 2 | | | | 3 | | | | |
| Octocrylene | | 3.6 | | | | | | | | 2 | | | | |
| Bis-Ethylhexyloxyphenol Methoxyphenyltriazine | 1 | 2 | 2 | | 2 | 3 | | 2 | | 1.5 | | 1 | 2 | 2 |
| Methylene Bis-benzotriazolyl tetramethylbutylphenol | 2 | | 3 | | 1 | | | | | | 1 | | | |
| 1,1'-(1,4-piperazinediyl)bis[1-[2-[4-(diethylamino)-2-hydroxybenzoyl] phenyl]-methanone | | | | | | | | | | | | 2 | 3 | 1 |
| Benzotriazoyl Dodecyl p-Cresol | | | | | | | | | | 3 | | | | |
| Butyloctyl Methoxycrylene | | 4 | | | | | | | | | | | | |
| Vitamin E Acetate | 0.2 | 0.2 | 0.2 | 0.3 | 0.1 | 0.5 | 0.3 | 0.1 | 0.5 | 0.1 | 0.5 | 0.2 | 0.2 | 0.1 |
| Disodium EDTA | 0.1 | 0.1 | 0.2 | 0.2 | 0.2 | 0.5 | 0.2 | 0.2 | 0.5 | 0.2 | 0.5 | 0.1 | 0.2 | 0.2 |
| Fragrance, Preservatives | q.s | q.s | q.s | q.s | q.s | q.s | q.s | q.s | q.s | q.s | q.s | q.s | q.s | q.s |
| Water | | | | | | | | ad 100 | | | | | | |

| Hydrodispersions | 1 | 2 | 3 | 4 | 5 | 6 | 7 | 8 | 9 |
|---|---|---|---|---|---|---|---|---|---|
| Glyceryl Stearate Citrate | | | 0.4 | | | | | | |
| Sodium Carbomer | | | | | 0.3 | | | | |
| Acrylates/C$_{10-30}$ Alkyl Acrylate Crosspolymer | | | 0.3 | 0.4 | 0.1 | 0.1 | 0.2 | 0.3 | 0.1 |
| Ceteareth-20 | | | 1 | | | | | | |
| Potassium Cetyl Phosphate | | | | | 2 | | | 1.5 | 2 |
| Xanthan Gun | 0.5 | | | 0.15 | | 0.5 | 0.2 | 0.2 | 0.2 |
| Dimethicone/Vinyl Dimethicone Crosspolymer | | | | 5 | | 3 | 1.5 | | |
| 2-(4-Diethylamino-2-hydroxybenzoyl)-benzoic Acid Hexylester | 0.25 | | | 0.5 | 2 | 1.5 | | | 1.5 |
| 2,4,6-Tribiphenyl-4-yl-1,3,5 Triazine | | | | | 3 | | 0.5 | | |
| Merocyanine | | 2 | | | | | | | 4 |
| Butyl Methoxydibenzoylmethane | 2 | | | 3.5 | | | 5 | | 2 |
| Ethylhexyl Bis-Isopentylbenzoxazolylphenyl Melamine | | | | 0.5 | | 2 | | | |
| Bis-Ethylhexyloxyphenol Methoxyphenyltriazine | | | 2 | | 0.25 | | | | 1 |
| Disodium Phenyl Dibenzimidazole Tetrasulfonate | 2 | | | | | 1 | | | |
| Phenylbenzimidazole Sulfonic Acid | | | | 2 | | | | | 0.5 |
| Ethylhexyl Methoxycinnamate | | | | 7 | | 5 | 8 | | |
| Diethylhexyl Butamido Triazone | | | | 2 | 2 | | | | |
| Ethylhexyl Triazone | | 4 | 3 | | | 4 | | 1 | 1 |
| Octocrylene | | 2 | | | | | | | |
| Polysilicone-15 | | | 0.9 | | | | | | 3 |
| Methylbenzylidene Camphor | | | | 3 | | 4 | | | |
| polyglycerol based UV filter according to the invention such as in particular the compound of example 1 or 2 | 1 | 2 | 4 | 0.75 | 5 | 8 | 10 | 25 | 15 |
| Titanium Dioxide | | 0.5 | 2 | 1 | 2 | 3 | 1 | 2 | |

| Hydrodispersions | 1 | 2 | 3 | 4 | 5 | 6 | 7 | 8 | 9 |
|---|---|---|---|---|---|---|---|---|---|
| Drometrizole Trisiloxane | | | | 1 | | 0.5 | | | |
| Terephthalidene Dicamphor Sulfonic Acid | | | | 0.5 | | 0.75 | | | |
| Benzotriazoyl Dodecyl p-Cresol | | | 3 | | | | 8 | | |
| $C_{12-15}$ Alkyl Benzoate | 2 | | 2.5 | | | | | 15 | 7.5 |
| Butylene Glycol Dicaprylate/Dicaprate | 4 | | | | 6 | | | 2 | |
| Dicaprylyl Carbonate | | 3 | | | | | | | 1.5 |
| Dicaprylylether | | 2 | | | | | | | |
| Cyclomethicone | | | | | 7.5 | | 3 | | |
| 2-Phenylethylbenzoate | | | | 4 | 2 | | | | |
| Diethylhexylnaphthalate | 5 | | | 6 | | | | | |
| Tridecylsalicylate | 2 | 3 | 1 | 5 | 3 | 0.5 | 3 | | |
| PVP Hexadecene Copolymer | 0.5 | | 0.5 | | 0.5 | 1 | | 0.5 | |
| Glycerin | 10 | 5 | 5 | | 5 | 8 | | 3 | 3 |
| Butylene Glycol | | | 7 | | | | | | |
| *Glycine Soja* | | | | 1 | | | 1 | | |
| Vitamin E Acetate | 0.5 | 0.25 | 0.5 | 0.25 | 0.75 | 1 | 0.25 | 0.75 | 0.5 |
| Alpha-Glycosylrutin | | | | | 0.25 | | | 0.25 | |
| Trisodium EDTA | | 0.1 | 0.1 | 0.1 | 0.2 | | 0.1 | 0.2 | 0.1 |
| Tromethamine | | | q.s. | | | | | | q.s. |
| Ethanol | 3 | 10 | 4 | 3.5 | 0.5 | 1 | | | |
| Preservatives | q.s | q.s | q.s | q.s | q.s | q.s | q.s | q.s | q.s |
| Fragrance, Colours | q.s | q.s | q.s | q.s | q.s | q.s | q.s | q.s | q.s |
| Water | | | | | ad 100 | | | | |

| Foams | 1 | 2 | 3 | 4 | 5 | 5 |
|---|---|---|---|---|---|---|
| Stearic Acid | 2 | 2 | | | | |
| Palmitic Acid | | | 1.5 | | 1.5 | 1.5 |
| Cetyl Alcohol | 2.5 | 2 | | 2 | | |
| Potassium Cetyl Phosphate | | | | 2 | 1.5 | 1.5 |
| Stearyl Alcohol | | | 3 | | 3 | 3 |
| PEG-100 Stearate | | | | 3.5 | | |
| PEG-40 Stearate | | 2 | | | | |
| PEG-20 Stearate | 3 | | | | | |
| Sorbitan Stearate | | 0.8 | | 0.5 | | |
| $C_{12-15}$ Alkyl Benzoate | 5 | | | | | 8 |
| $C_{12-13}$ Alkyl Tartrate | | | 7 | | 7 | |
| Butyleneglycol Dicaprylate/Dicaprate | | 6 | | 5 | | |
| Dicaprylyl Ether | | | 2 | | 2 | 2 |
| Cyclomethicone | | 2 | 3 | | 3 | |
| Butylene Glycol | 1 | | | | | 3 |
| Isohexadecane | 2 | | | | | |
| Methylpropandiol | | | | | | |
| Propylene Glycol | | | 5 | | 5 | |
| Glycerin | 5 | 7 | | 3 | | |
| 2-(4-Diethylamino-2-hydroxybenzoyl)-Benzoic Acid Hexylester | 2 | | | | | |
| Merocyanine | | | | | 2.4 | |
| Butyl Methoxydibenzoylmethane | | | 2 | 3 | | 4 |
| Dimethicodiethylbenzalmalonate | | | 3 | | | |
| Homosalate | | | 5 | | | 5 |
| Phenylbenzimidazole Sulfonic Acid | | | 2 | 2 | | |
| Benzophenone-3 | 2 | | | | | |
| Ethylhexyl Salicylate | | | 5 | 3 | | |
| Octocrylene | 2 | | | 3 | | |
| Bis-Ethylhexyloxyphenol Methoxyphenyltriazine | | | 3 | 1 | | |
| 2,2 Methylen-bis-(6(2H-benzotriazol-2-yl)-4-(1,1,3,3-tetramethylbutyl)phenol | | | | 8 | | |
| 2,4,6-Tribiphenyl-4-yl-1,3,5 Triazine | | | 5 | 0.5 | | |
| polyglycerol based UV filter according to the invention such as in particular the compound of example 1 or 2 | 3 | 6 | 10 | 15 | 20 | 20 |
| $C_8$-$C_{16}$ Alkylpolyglycoside | 1 | | | | | |
| Vitamin E Acetate | 0.6 | 0.5 | 0.2 | 0.5 | 0.2 | 0.2 |
| Creatine/Creatinine | | | 0.5 | | 0.5 | 0.5 |
| BHT | | | 0.1 | | 0.1 | 0.1 |
| Disodium EDTA | 0.5 | | | | | |
| Fragrance, Preservatives | q.s | q.s | q.s | q.s | q.s | q.s |
| Colours | q.s | q.s | q.s | q.s | q.s | q.s |
| Sodium Hydroxide | q.s | | | | q.s | q.s |
| Potassium Hydroxide | | | | q.s | | |
| Tromethamine | | | q.s | q.s | | |
| Water | | | | ad 100 | | |

EXAMPLE 1

Preparation of a Polymeric UV-Filter by Attaching p-dimethylamino Benzoic Acid to poly(glycerol-b-propylene oxide): PG-UVB1

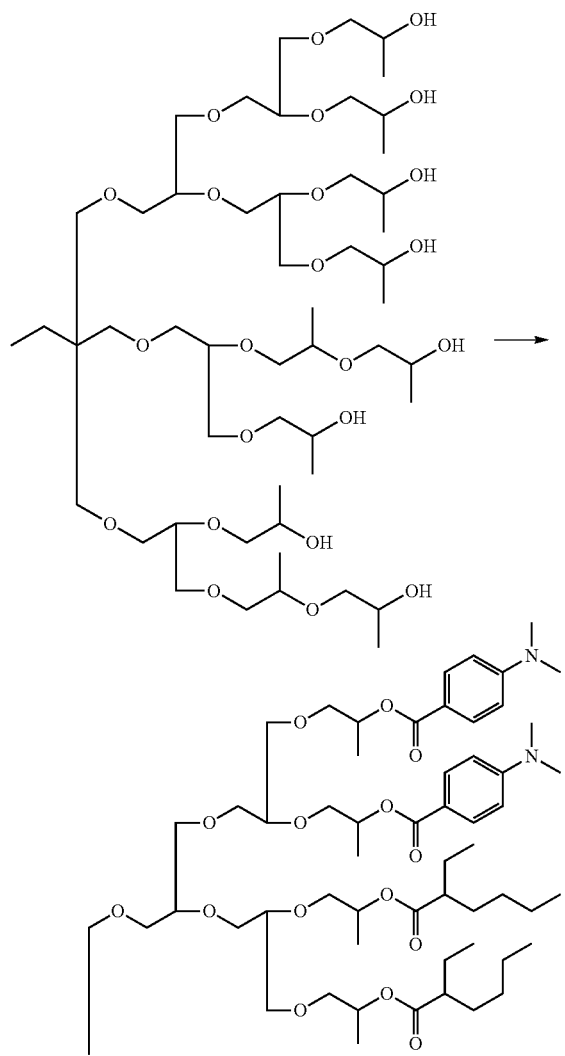

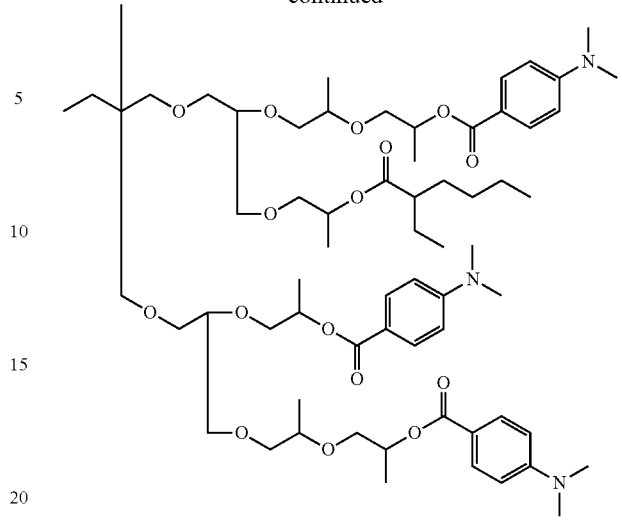

Poly(glycerol-b-propylene oxide) was prepared according to Sunder, A.; Mulhaupt, R.; Frey, H. *Macromolecules,* 2000, 33, 309-314.

To a solution of poly(glycerol-b-propylene oxide) (15.0 g, 111 mmol OH) in pyridine (300 mL) p-dimethylamino benzoic acid chloride (15.5 g, 84 mmol, 75% loading) is added and the reaction mixture is stirred at 115° C. for 12 h. The reaction mixture is cooled to 80° C. and 2-ethyl hexanoic acid chloride (5.4 g, 33 mmol) is added. The reaction mixture is stirred at 115° C. for 4 h and evaporated to dryness. The residue is dissolved in toluene and extracted with 10% aqueous potassium carbonate, 5% aqueous citric acid, and brine. The organic layer is dried over sodium sulfate, filtered, and evaporated to dryness. After removal of residual solvents at 80° C. under high vacuum for 12 h 29.6 g product is obtained as a highly viscous polymeric UVB filter.

The polymeric filter shows typically an $E_{1/1}$-value of 730 in THF at 306 nm. The solubility in Finsolv TN (INCI $C_{12-15}$ alkyl benzoate) is determined to be at least 50% (w/w).

EXAMPLE 2

Preparation of a Polymeric UV-Filter by Attaching p-dimethylamino Benzoic Acid to poly(glycerol-b-propylene oxide): PG-UVB2

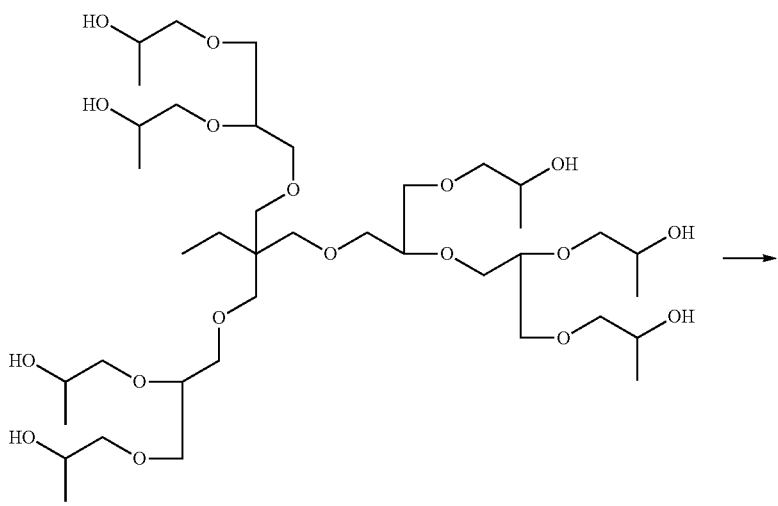

-continued

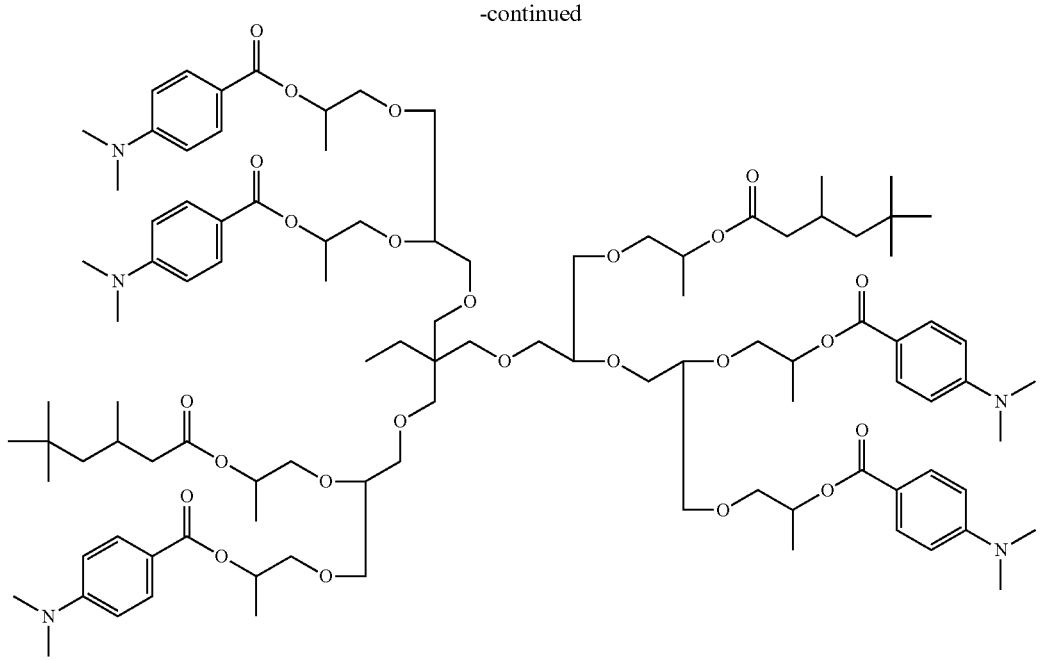

Poly(glycerol-b-propylene oxide) was prepared according to Sunder, A.; Mulhaupt, R.; Frey, H. *Macromolecules*, 2000, 33, 309-314.

To poly(glycerol-b-propylene oxide) (5.0 g, 38 mmol OH) is added sequentially a catalytical amount of potassium tert. butoxide and p-dimethylamino benzoic acid ethyl ester (5.6 g, 29 mmol, 75% loading). The reaction mixture is stirred at 160° C. for 4 h while evolving ethanol is removed under vacuo. 3,5,5-trimethylhexanoyl chloride (3.2 g, 18 mmol) is added dropwise. The reaction mixture is stirred at 160° C. for 2 h. Excess of acid chloride is removed under vacuo and the reaction mixture is cooled to room temperature. A highly viscous polymeric UVB filter is obtained, which shows typically an $E_{1/1}$-value of 730 in THF at 308 nm. The solubility in Finsolv TN (INCI $C_{12-15}$ alkyl benzoate) is determined to be at least 50% (w/w).

EXAMPLE 3

Solubility

The solubility of BMDBM (Butyl Methoxydibenzoylmethane, Parsol® 1789) and BEMT (bis-ethylhexyloxyphenol methoxyphenyl triazine, Tinosorb® S) in the cosmetic solvent $C_{12-15}$ alkyl benzoate was determined by standard methods (saturation of the solvent with BMDBM or BEMT and determination of the content of BMDBM or BEMT in the supernatant by HPLC) and resulted in solubility values of 14 respectively 13 wt.-% which are in line with the values given by the suppliers (Merck/CIBA).

PG-UVB1 and PG-UVB2 are due to their high viscosity not free flowing and can therefore not be used as solvent for solid UV absorbers such as BMDBM and BEMT itself.

The solubility of BMDBM in a 1:1 (w/w) mixture of $C_{12-15}$ alkyl benzoate/PG-UVB1 of example 1 as well as in a 1:1 (w/w) mixture of $C_{12-15}$ alkyl benzoate/PG-UVB2 of example 2 was determined by saturation of the respective 1:1 mixture with BMDBM at room temperature and determination of the BMDBM concentration of the supernatant by HPLC to be 188 mg/g, respectively 180 mg/g.

The solubility of BEMT in a 1:1 (w/w) mixture of $C_{12-15}$ alkyl benzoate/PG-UVB1 of example 1 was determined by saturation of the respective 1:1 mixture with BMDBM at room temperature and determination of the BMDBM concentration of the supernatant by HPLC to be 292 mg/g.

| Solubility of | BMDBM | BMDBM | BEMT |
|---|---|---|---|
| in $C_{12-15}$ alkyl benzoate | 14 wt.-% | 14 wt.-% | 13 wt.-% |
| in $C_{12-15}$ alkyl benzoate/ PG-UVB1 1:1 | 19 wt.-% | — | 29 wt.-% |
| in $C_{12-15}$ alkyl benzoate/ PG-UVB2 1:1 | — | 18 wt.-% | — |
| Δ solubility | +5 wt.-% | +4 wt.-% | 16 wt.-% |
| Increase of solubility BMDBM/BEMT | +36% | +29% | +123% |
| Δ solubility relating to cosmetic solvent | +12 wt.-% | +11 wt.-% | +22.5 wt.-% |

As can be retrieved from the results, the solubility of BMDBM, respectively BEMT in $C_{12-15}$ alkyl benzoate can be significantly enhanced by the use of PG-UVB1, respectively PG-UVB2 as solubility enhancer.

EXAMPLE 4

Reduction of Solvent Necessary to Dissolve Solid UV-Filter a.) 2.0 g of diisopropyl sebacate are necessary to solubilize 0.5 g BMDBM. However, only 1.4 g of a 1:1 (w/w) mixture of PG-UVB1 of example 1 and diisopropyl sebacate is needed to dissolve 0.5 g BMDBM resulting in a reduction of the cosmetic solvent necessary to dissolve BMDBM of 65%.

b) 3.0 g of $C_{12-15}$ alkyl benzoate are necessary to solubilize 0.5 g BMDBM, whereas only 1.5 g of a 1:1 (w/w) mixture of PG-UVB2 of example 2 and $C_{12-15}$ alkyl benzoate is necessary to dissolve 0.5 g of BMDBM resulting in a reduction of the cosmetic solvent necessary to dissolve BMDBM of 75%.

EXAMPLE 4

Comparative Example

4a) Preparation of a Polymeric UV-Filter by Attaching p-dimethylamino benzoic acid and 2-(4-diethylamino-2-hydroxybenzoyl)benzoic acid to Hybrane® S1200: HY-AB

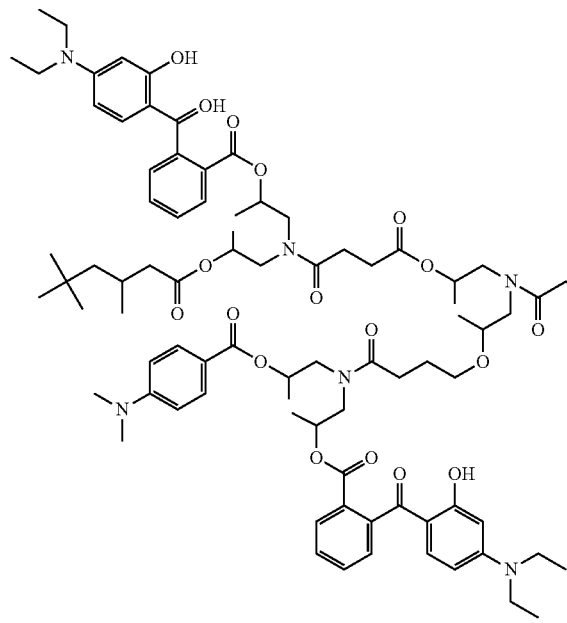

Hybrane® S1200 (WO 99/16810) was supplied from DSM Hybrane (Geleen, The Netherlands) with a Mn of about 1200 g/mol as determined by GPC.

A mixture of Hybrane® S1200 (5.0 g, 4.2 mmol, 33.0 mmol OH), 2-(4-diethylamino-2-hydroxybenzoyl)benzoic acid methyl ester (3.6 g, 11 mmol), 1,8-diazabicyclo[5.4.0]undec-7-ene (0.5 g, 3 mmol), and diglyme (2.5 g) is stirred at 160° C. for 3 hours while argon is flushed continuously through the reaction mixture. 4-(dimethylamino)benzoyl chloride (2.2 g, 12 mmol) is added and the reaction mixture is stirred at 160° C. for another 2 hours. The mixture is cooled to room temperature and solved in pyridine (20 mL). 3,5,5-trimethylhexanoyl chloride (1.9 g, 10 mmol) is added and the reaction mixture is stirred at room temperature for 4 hours. Excess acid chloride is hydrolyzed by addition of water (1 mL) and stirring for another hour at room temperature. Ethyl acetate (100 mL) is added followed by extractions with 10 w % aqueous potassium carbonate solution (100 mL), 5 w % aqueous citric acid solution (100 mL) and brine (100 mL). The combined organic extracts are dried over sodium sulfate, filtered and evaporated under vacuo to yield 6.4 g HY-AB.

4b.) Preparation of a Polymeric UVB-Filter: HY-B1

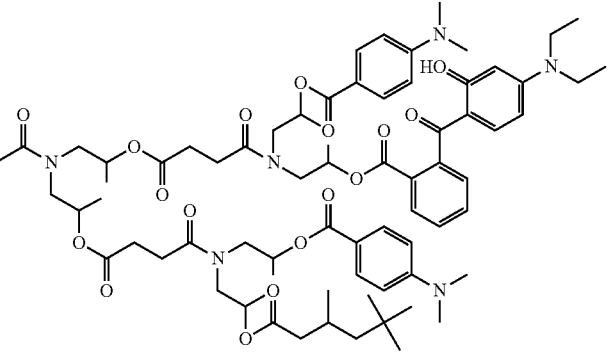

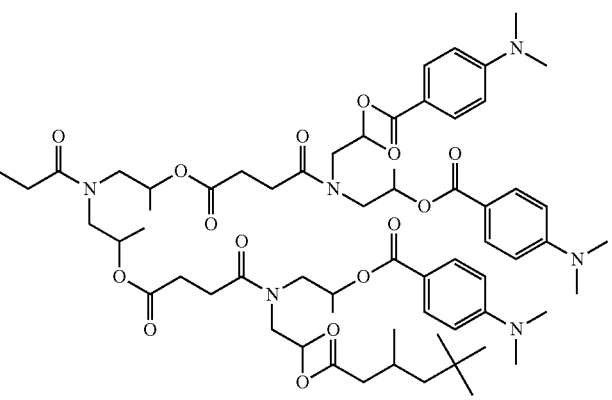

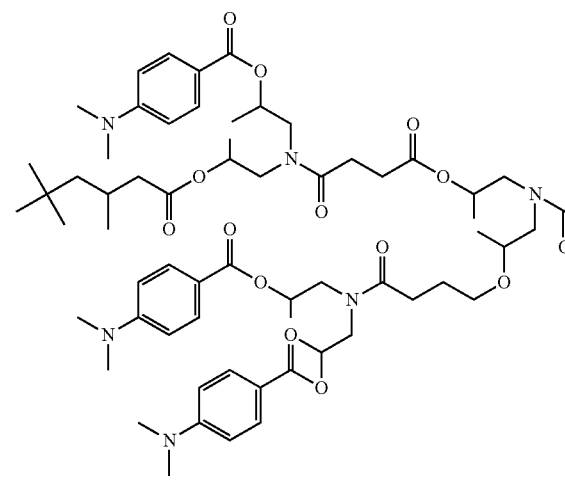

Hybrane® S1200 (WO 99/16810) was supplied from DSM Hybrane (Geleen, The Netherlands) with a Mn of about 1200 g/mol as determined by GPC.

4-(dimethylamino)benzoyl chloride (4.6 g, 25 mmol) is added to a solution of Hybrane® S1200 (5.0 g, 4.2 mmol, 33.0 mmol OH) in pyridine (20 mL) and stirred under reflux for one hour. 3,5,5-trimethylhexanoyl chloride (1.6 g, 9 mmol) is added and the reaction mixture is stirred under reflux for another 4 hours. Excess acid chloride is hydrolyzed by addition of water (1 mL) and stirring for another hour at room temperature. Ethyl acetate (100 mL) is added followed by extractions with 10 w % aqueous potassium carbonate solution (100 mL), 5 w % aqueous citric acid solution (100 mL) and brine (100 mL). The combined organic extracts are dried over sodium sulfate, filtered and evaporated under vacuo to yield 5.2 g HY-B1.

4c.) Preparation of a Polymeric UVB-Filter: HY-B2

Subsequently a solution of 4-(dimethylamino)benzoyl chloride (4.5 g, 24 mmol) in DCM (25 mL) is added dropwise keeping the temperature below 5° C. The reaction mixture is stirred at room temperature for 48 h. Excess acid chloride is hydrolyzed by addition of water (100 mL) and stirring for another 12 h at room temperature. The phases are separated and the aqueous phase is extracted with DCM (2×50 mL). The combined organic phases are washed with saturated bicarbonate solution (150 mL) and 2 N HCl (150 mL). Each organic phase is re-extracted with DCM (50 mL). The combined organic extracts are dried over sodium sulfate, filtered and evaporated under vacuo. The oily residue is purified over column chromatography (ethyl acetate/n-hexane, 1:2 ⇒ ethyl acetate) on silica to yield 6.46 g HY-B2.

Solubility

The solubility of BMDBM in a 1:1 (w/w) mixture of $C_{12-15}$ alkyl benzoate and a polymeric, respectively a solid UV-filter

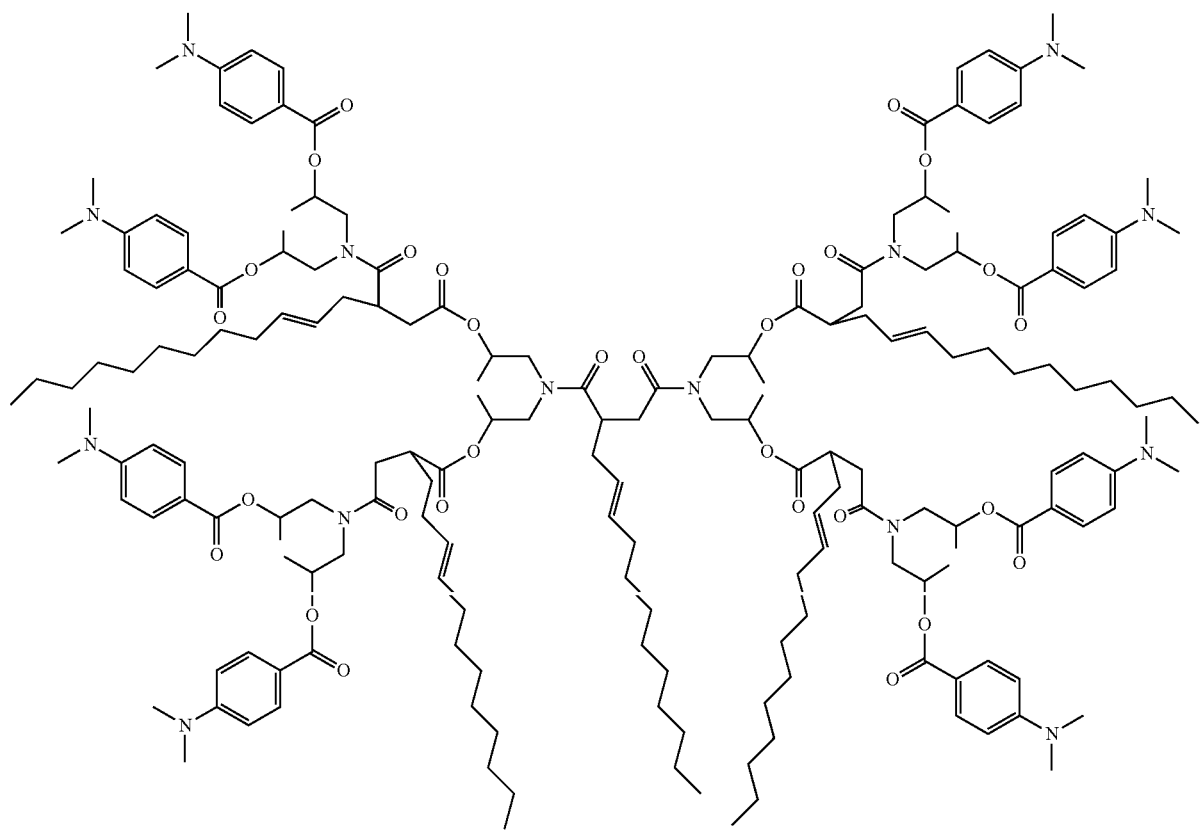 [SMILES: CCCCCCCC/C=C/CCC(CC(=O)N(CC(C)OC(=O)c1ccc(N(C)C)cc1)CC(C)OC(=O)c1ccc(N(C)C)cc1)C(=O)OC(C)CN(CC(C)OC(=O)CC(C/C=C/CCCCCCCCC)C(=O)N(CC(C)OC(=O)c1ccc(N(C)C)cc1)CC(C)OC(=O)c1ccc(N(C)C)cc1)C(=O)C(C/C=C/CCCCCCCCC)CC(=O)N(CC(C)OC(=O)C(C/C=C/CCCCCCCCC)CC(=O)N(CC(C)OC(=O)c1ccc(N(C)C)cc1)CC(C)OC(=O)c1ccc(N(C)C)cc1)CC(C)OC(=O)C(C/C=C/CCCCCCCCC)CC(=O)N(CC(C)OC(=O)c1ccc(N(C)C)cc1)CC(C)OC(=O)c1ccc(N(C)C)cc1]

Hybrane® D2000 (WO 99/16810) was supplied from DSM Hybrane (Geleen, The Netherlands) with a Mn of about 2000 g/mol as determined by GPC.

Triethylamine (4.0 mL, 29.0 mmol) and DMAP (50 mg) is added to a solution of Hybrane® D2000 (5.0 g, 2.5 mmol, 20.0 mmol OH) in DCM (75 mL) under Argon at 0° C.

(i.e. Polysilicone-15 (P-15), HY-B1, HY-B2, HY-AB, BEMT or Ethylhexyltriazone (EHT)) was determined by mixing 200 mg of BMDBM with 1000 mg of the 1:1 mixture and measuring the BMDBM concentration of the supernatant by HPLC after a storage period of 1 month at RT. Where necessary the mixture was centrifuged in order to obtain a clear supernatant. The results are summarized in the table below.

| Solubility of BMDBM | UV-filter in 1:1 mixture | | | | | |
|---|---|---|---|---|---|---|
| | P-15 | HY-AB | HY-B1 | HY-B2 | BEMT | EHT |
| in $C_{12-15}$ alkyl benzoate | 14 wt.-% | 14 wt.-% | 14 wt.-% | 14 wt.-% | 14 wt.-% | n.a. |
| in $C_{12-15}$ alkyl benzoate/UV-filter 1:1 | 6 wt.-% | 7 wt.-% | 6 wt.-% | 7 wt.-% | 3 wt.-% | n.a. |
| Δ solubility | −8 wt.-% | −7 wt.-% | −8 wt.-% | −7 wt.-% | −11 wt.-% | n.a. |
| Δ solubility related to cosmetic solvent | −1 wt.-% | ±0 wt.-% | −1 wt.-% | ±0 wt.-% | −4 wt.-% | n.a. | n.a: not analyzable

As can be retrieved from the results, the solubility of BMDBM in $C_{12-15}$ alkyl benzoate can neither be enhanced by a silicone based polymeric UV-filter (polysilicone-15), a Hybrane based UV-filter (HY-AB, HY-B1, HY-B2) nor a solid UV-filter (BEMT or EHT).

The invention claimed is:

1. A method to enhance solubility of butyl methoxydibenzoylmethane and/or bis-ethylhexyloxyphenol methoxyphenyl triazine in cosmetic oils suitable as solvents for butyl methoxydibenzoylmethane and/or bis-ethylhexyloxyphenol methoxyphenyl triazine which comprises adding a solubility enhancing effective amount of a polyglycerol-based UV filter to a composition comprised of butyl methoxydibenzoylmethane and/or bis-ethylhexyloxyphenol methoxyphenyl triazine and a cosmetic oil suitable as a solvent therefore, wherein the polyglycerol-based UV filter is obtained by a process comprising the steps of:

a) ring-opening polymerization of x mol equivalents of glycidol using 1 mol equivalent of a polyol starter unit with y mol equivalents hydroxyl-groups, followed by b) block copolymerization with z X (x+y) mole equivalents of propyleneoxide to form a hyperbranched polyether-polyol backbone carrying (x+y) mol equivalents hydroxyl-groups, followed by c) partial or total esterification of the hydroxyl groups with p-dimethylamino benzoic acid, wherein x is an integer from 3-16, y is an integer from 1-6, and z is an integer from 0-10, wherein 30 to 80% of the hydroxyl groups of the hyperbranched polyether-polyol backbone are esterified with p-dimethylamino benzoic acid, and wherein residual terminal hydroxyl groups are linked to a capping group which is a 2-ethylhexanoyl group, an acetyl group and/or a 3,5,5-trimethylhexanoyl group; and wherein the cosmetic oil is diisopropyl sebacate or a C12-15 alkyl benzoate.

2. The method according to claim 1, wherein about 60 to 75% of the hydroxyl groups of the hyperbranched polyether-polyol backbone are esterified with p-dimethylamino benzoic acid.

3. The method according to claim 1, wherein the amount of glycidol units x is selected in the range of 3 to 16 mol equivalents per mol equivalent of the polyol starter unit.

4. The method according to claim 1, wherein the polyol starter unit is trimethylolpropane.

5. The method according to claim 1, wherein 60-75% of the terminal hydroxyl groups of the hyperbranched polyether-polyol backbone are linked to a p-dimethylamino benzoyl moiety.

\* \* \* \* \*